(12) United States Patent
Folger et al.

(10) Patent No.: US 9,289,390 B2
(45) Date of Patent: Mar. 22, 2016

(54) TASTE MASKED PHARMACEUTICAL COMPOSITION

(71) Applicants: Martin Folger, Ingelheim am Rhein (DE); Stefan Lehner, Wiesbaden (DE); Annette Grave, Loerrach (DE); Norbet Poellinger, Muellheim (DE); Randolph Seidler, Eckenroth (DE)

(72) Inventors: Martin Folger, Ingelheim am Rhein (DE); Stefan Lehner, Wiesbaden (DE); Annette Grave, Loerrach (DE); Norbet Poellinger, Muellheim (DE); Randolph Seidler, Eckenroth (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 0 days.

(21) Appl. No.: 14/254,136

(22) Filed: Apr. 16, 2014

(65) Prior Publication Data

US 2014/0227351 A1     Aug. 14, 2014

Related U.S. Application Data

(62) Division of application No. 13/584,806, filed on Aug. 13, 2012, now Pat. No. 8,741,350.

(30) Foreign Application Priority Data

Aug. 12, 2011  (EP) ..................................... 11177354

(51) Int. Cl.
*A61K 9/24*   (2006.01)
*A61K 9/16*   (2006.01)
(Continued)

(52) U.S. Cl.
CPC ................. *A61K 9/1676* (2013.01); *A61K 8/73* (2013.01); *A61K 9/0056* (2013.01);
(Continued)

(58) Field of Classification Search
CPC .... A61K 8/73; A61K 38/005; A61K 38/0051
See application file for complete search history.

(56) References Cited

U.S. PATENT DOCUMENTS 3,708,485 A   1/1973   Stahle et al.
4,361,563 A   11/1982  Austel et al.
(Continued)

FOREIGN PATENT DOCUMENTS

CA   1185239 A1   4/1985
CA   1287226 C    8/1991
(Continued)

OTHER PUBLICATIONS

Cervetto, et al., "Effects of Blocking the Rod Hyperpolarization Activated Current on the Flash ERG". Investigative Ophthalmology & Visual Science, vol. 37, No. 3, Feb. 1996, Abstract 1598-B501, p. S347.
(Continued)

*Primary Examiner* — Carlos Azpuru
(74) *Attorney, Agent, or Firm* — Michael P. Morris; Wendy M. Gombert

(57) ABSTRACT

Taste masked multi-layered particles include an inert core, one or more coating layer(s) comprising a pharmaceutically active ingredient and a binder, an intermediate coating layer (seal coating) free from a low molecular weight water-soluble ionic compound and including a water-soluble pharmaceutical film-forming compound selected from (i) HPMC and PEG or (ii) PVP, and an outer coating layer (final or taste masking coating) free from a low molecular weight water-soluble ionic compound and comprising (i) a poly(meth)acrylate or (ii) a mixture including 60-90% (w/w) EC and 10-40% (w/w) HPMC, where the pharmaceutically active ingredient is water-soluble and includes either at least one basic group and/or a bitter taste. Further disclosed are methods for the production of such particles and pharmaceutical compositions including such particles.

9 Claims, 4 Drawing Sheets

(51) Int. Cl.

| | | |
|---|---|---|
| *A61K 8/73* | (2006.01) | |
| *A61K 38/00* | (2006.01) | |
| *A61K 9/20* | (2006.01) | |
| *A61K 9/50* | (2006.01) | |
| *A61K 31/501* | (2006.01) | |
| *A61K 31/522* | (2006.01) | |
| *A61K 31/5415* | (2006.01) | |
| *A61K 31/55* | (2006.01) | |
| *A61K 9/00* | (2006.01) | |
| *A61K 31/00* | (2006.01) | |
| *A61K 31/4168* | (2006.01) | |
| *A61K 9/28* | (2006.01) | |

(52) U.S. Cl.
  CPC ............ *A61K 9/0095* (2013.01); *A61K 9/1635* (2013.01); *A61K 9/1652* (2013.01); *A61K 9/2072* (2013.01); *A61K 9/2893* (2013.01); *A61K 9/5026* (2013.01); *A61K 9/5047* (2013.01); *A61K 9/5078* (2013.01); *A61K 9/5089* (2013.01); *A61K 31/00* (2013.01); *A61K 31/4168* (2013.01); *A61K 31/501* (2013.01); *A61K 31/522* (2013.01); *A61K 31/5415* (2013.01); *A61K 31/55* (2013.01); *A61K 38/005* (2013.01)

(56) References Cited

U.S. PATENT DOCUMENTS

| | | | |
|---|---|---|---|
| 4,611,008 | A | 9/1986 | Heinzelmann |
| 4,874,613 | A | 10/1989 | Hsiao |
| 4,980,175 | A | 12/1990 | Chavkin et al. |
| 5,175,157 | A | 12/1992 | Psiorz et al. |
| 5,296,482 | A | 3/1994 | Peglion et al. |
| 5,308,853 | A | 5/1994 | Hodges et al. |
| 5,516,773 | A | 5/1996 | Rose |
| 5,595,987 | A | 1/1997 | Lasker et al. |
| 5,721,217 | A | 2/1998 | Liu et al. |
| 5,760,069 | A | 6/1998 | Lukas-Laskey et al. |
| 5,840,329 | A | 11/1998 | Bai |
| 5,954,049 | A | 9/1999 | Foley et al. |
| 5,968,978 | A | 10/1999 | Kleemann et al. |
| 6,083,991 | A | 7/2000 | Bergeron, Jr. |
| 6,136,347 | A | 10/2000 | Pollinger et al. |
| 6,204,281 | B1 | 3/2001 | Webb et al. |
| 6,395,728 | B2 | 5/2002 | Webb et al. |
| 6,573,279 | B1 | 6/2003 | Watanabe et al. |
| 7,208,508 | B2 | 4/2007 | Daemmgen et al. |
| 7,829,748 | B1 | 11/2010 | Tung et al. |
| 8,106,060 | B2 | 1/2012 | Pfrengle et al. |
| 8,741,350 | B2 | 6/2014 | Folger et al. |
| 2004/0014795 | A1 | 1/2004 | Daemmgen et al. |
| 2004/0127846 | A1 | 7/2004 | Dunn et al. |
| 2004/0138306 | A1 | 7/2004 | Guth et al. |
| 2004/0266869 | A1 | 12/2004 | Montague et al. |
| 2005/0287211 | A1 | 12/2005 | Yoshida et al. |
| 2006/0063840 | A1 | 3/2006 | Guth et al. |
| 2006/0069073 | A1 | 3/2006 | Pieper et al. |
| 2006/0100278 | A1 | 5/2006 | Cooper et al. |
| 2006/0293293 | A1 | 12/2006 | Muller et al. |
| 2007/0054838 | A1 | 3/2007 | Stark et al. |
| 2007/0098746 | A1 | 5/2007 | Nichols et al. |
| 2007/0117783 | A1 | 5/2007 | Brueck-Scheffler |
| 2007/0142354 | A1 | 6/2007 | Guth et al. |
| 2008/0041369 | A1 | 2/2008 | Radau et al. |
| 2008/0041370 | A1 | 2/2008 | Radau et al. |
| 2008/0312210 | A1 | 12/2008 | Guth et al. |
| 2012/0058980 | A1 | 3/2012 | Radau et al. |
| 2013/0317008 | A1 | 11/2013 | Guth et al. |
| 2014/0171415 | A1 | 6/2014 | Kley et al. |
| 2014/0179651 | A1 | 6/2014 | Albrecht et al. |
| 2014/0224680 | A1 | 8/2014 | Folger et al. |

FOREIGN PATENT DOCUMENTS

| | | |
|---|---|---|
| CA | 1321194 C | 8/1993 |
| CA | 2435526 A1 | 1/2004 |
| CA | 2555050 A1 | 9/2005 |
| DE | 3541811 A1 | 6/1987 |
| EP | 0008391 A1 | 3/1980 |
| EP | 0065229 A1 | 11/1982 |
| EP | 0137978 A2 | 4/1985 |
| EP | 0224794 A2 | 6/1987 |
| EP | 0292840 A2 | 11/1988 |
| EP | 0330052 A2 | 8/1989 |
| EP | 0409254 A1 | 1/1991 |
| EP | 0471388 A2 | 2/1992 |
| EP | 0534859 A1 | 3/1993 |
| EP | 0551820 A1 | 7/1993 |
| EP | 1276476 A2 | 1/2003 |
| EP | 1362590 A1 | 11/2003 |
| EP | 1534296 A1 | 6/2005 |
| EP | 1762179 A1 | 3/2007 |
| EP | 2098225 A2 | 9/2009 |
| EP | 2127643 A1 | 12/2009 |
| EP | 2298288 A1 | 3/2011 |
| JP | 2000355577 A | 12/2000 |
| JP | 2004264195 A | 9/2004 |
| JP | 2006327943 A | 12/2006 |
| JP | 2007015966 A | 1/2007 |
| JP | 2008081448 A | 4/2008 |
| RU | 2078536 C1 | 5/1997 |
| WO | 9712689 A1 | 4/1997 |
| WO | 9836732 A2 | 8/1998 |
| WO | 0002543 A2 | 1/2000 |
| WO | 0075133 A1 | 12/2000 |
| WO | 0178699 A2 | 10/2001 |
| WO | 03075895 A1 | 9/2003 |
| WO | 2004011006 A1 | 2/2004 |
| WO | 2005004851 A1 | 1/2005 |
| WO | 2005084647 A1 | 9/2005 |
| WO | 2005085246 A1 | 9/2005 |
| WO | 2006046256 A1 | 5/2006 |
| WO | 2006074185 A2 | 7/2006 |
| WO | 2007014886 A1 | 2/2007 |
| WO | 2007100779 A2 | 9/2007 |
| WO | 2008027993 A2 | 3/2008 |
| WO | 2008075372 A1 | 6/2008 |
| WO | 2009011967 A1 | 1/2009 |
| WO | 2010007515 A2 | 1/2010 |
| WO | 2011039768 A2 | 4/2011 |
| WO | 2011098582 A2 | 8/2011 |
| WO | 2011117295 A1 | 9/2011 |

OTHER PUBLICATIONS

Ragueneau, et al., "Pharmacokinetic-pharmacodynamic modeling of the effects of ivabradine, a direct sinus node inhibitor, on heart rate in healthy volunteers". Clinical Pharmacology & Therapeutics, vol. 64, No. 2, Aug. 1998, pp. 192-203.

Raes et al., "Use-dependent block of Ih in mouse dosal root ganglion neurons by sinus node inhibitors". British Journal of Pharmacology, vol. 125, 1998, pp. 741-750.

Pape, H.C., "Specific Bradycardic Agents Block the Hyperpolarization-Activated Cation Current in Central Neurons". Neuroscience, vol. 59, No. 2, 1994, pp. 363-373.

Shinke et al., "Beneficial Effects of Heart Rate Reduction on Cardia Mechanics and Energetics in Patients With Left Ventricular Dysfunction". Japanese Circulation Journal, vol. 63, No. 12, Dec. 1999, pp. 957-964.

Katz, Arnold M., "Maladaptive Growth in the Failing Heart: The Cardiomyopathy of Overload"., Cardivascular Drusts and Therapy, vol. 16, May 2002, pp. 245-249.

Maron, Barry J., "Hypertrophic Cardiomyopathy: A Systematic Review". The Journal of American Medical Association, vol. 287, No. 3, Mar. 2002, pp. 1308-1320.

"Hypertrophic Cardiomyopathy"., The Merck Manual of Diagnosis and Therapy, 15th Edition, Merck Sharp & Dohme Research Laboratories, Rahway, N.J. 1987, pp. 519-522.

(56) References Cited

OTHER PUBLICATIONS

Rieu et al., "Synthesis and bradycardic activitiy of a series of substituted 3-aminoalkyl-2,3-dihydro-4H-1,3-benzoxazin-4-ones as potent antiischemics". European Journal of Medicinal Chemistry, vol. 28, 1993, pp. 683-391.
Muller et al., "Combination of a Calcium Antagonist, Verapamil, with an Angiotensin Converting Enzyme Inhibitor, Trandolapril, in Experimental Myocardial Ischemia and Reperfusion: Antiarrhythmic and Hemodynamic Effects of Chronic Oral Pretreatment". Cardiovascular Drugs and Therapy, vol. 12, 1997, pp. 449-455.
Merck Index, 12th Edition, 1996, p. 541 and p. 1696.
Lijnen et al., "Renin-Angiotensin System, Hypertrophy and Gene Expression in Cardiac Myocytes". Journal of Molecular and Cellular Cardiology, vol. 31, 1999, pp. 949-970.
Hartmann et al., "Persisting Effect of Ca2+—Channel Blockers on Left Ventricular Function in Hypertrophic Cardiomyopathy After 14 Years' Treatment". Angiology: The Journal of Vascular Diseases, vol. 47, No. 8, Aug. 1996, pp. 765-773.
Kober et al., "Clinical Cardiology: Hypertrophic Cardiomopathy, Tuesday Afternoon. Long-term Verapamil vs Propranolol Treatement of Hypertrophic Cardiomyopathy in Matched Pairs of Patients". Circulation Supplement, Abstracts from the 60th Scientific Session, vol. 76, Supp. IV, Oct. 1987, p. IV-248, Abstract 0988.
International Search Report and Written Opinion for PCT/EP2003/07929 mailed Oct. 9, 2003.
Abstract in English for RU2078536, May 10, 1997, Derwent.
Berkow et al., "Hypertrophic Cardiomyopathy". The Merck Manual of Diagnosis and Therapy, Fifteenth Edition, Chapter 27, Merck Sharp & Dohme Research Laboratories, Rahway, NJ, 1987, pp. 519-522.
Epstein et al., "Verapamil: Its Potential for Causing Serious Complications in Patients with Hypertrophic Cardiomyopathy". Circulation: An Official Journal of the American Heart Association, Inc.®, vol. 64, No. 3, Sep. 1981, pp. 437-441.
Goodman & Gilman's The Pharmacological Basis of Therapeutics, Tenth Edition, McGraw-Hill Medical Publishing Division, New York, Ch. 3, Section 1, 2001, pp. 54-57.
Granetzny et al., "Pharmacologic Heart Rate Redution: Effect of a Novel, Specific Bradycardic Agent on the Heart". The Thoracic and Cardiovascular Surgeon, vol. 46, 1998, pp. 63-69.
Gregor et al., "Use of Verapamil in the Treatment of Hypertrophic Cardiomyopathy". Cor et Vasa, vol. 28, No. 6, 1986, pp. 404-412.
Kober et al., "Clinical Cardiology: Hypertrophic Cardiomyopathy; Tuesday Afternoon; Long-Term Verapamil vs Propranolol Treatment of Hypertrophic Cardiomyophathy in Matched Pairs of Patients". Circulation, Abstracts, vol. 76, Supp IV, Oct. 1987, p. IV-248.
Lei et al., "Bradycardia induces angiogenesis, increases coronary reserve, and preserves function of the postinfarcted heart". Circulation: Journal of the American Heart Association, vol. 110, Aug. 2004, pp. 796-802.
Martindale, et al., The Extra Pharmacopoeia, 30th Edition, The Pharmaceutical Press, London, Jan. 1993, p. 668.
Nicholls et al., "Cardiovascular Effects of Alinidine and Propranolol Alone and in Combination with Hydralazine in Normal Man". British Journal of Clinical Pharmacology, vol. 15, No. 1, 1983, pp. 21-29.
Ruschitzka et al., "Combination of ACE Inhibitors and Calcium Antagonists: A Logical Approach". Journal of Cardiovascular Pharmacology, vol. 31, Supp. 2, 1998, pp. S5-S16.
Toshima et al., "Comparable Effects of Oral Diltiazem and Verapamil in the Treatment of Hypertrophic Cardiomyopathy: Double-blind Crossover Study". Japanese Heart Journal, vol. 27, No. 5, 1986, pp. 710-715.
Abstract in English of EP0330052, Aug. 30, 1989.
Ilgenli et al., "Bisoprolol Improves Echocardiographic Parameters of Left Ventricular Diastolic Function in Patients with Systemic Hypertension". Cardiology, vol. 106, No. 3, 2006, pp. 127-131.
Myreng et al., "Effects of verapamil on left ventricular relaxation and filling dynamics in coronary artery disease: A study by pulsed Doppler echocardiography". American Heart Journal, vol. 117, No. 4, Apr. 1989, pp. 870-875.

Osipov et al., "Study of hemodynamic effects of allapinin and metoprolol using continuous wave Doppler echocardiography at rest and during physical exercise in patients with paroxysmal supraventricular tachycardia". Kardiologiia, vol. 31, No. 8, Aug. 1991, pp. 83-86. [Abstract Only, Medline].
Wakita et al., "The relationship between the improvement of cardiac function and the myocardial uptake of I-123 metaiodobenzylguanidine in patients with dilated cardiomyopathy treated by beta-blocker". Journal of Cardiology, vol. 26, No. 3, Sep. 1995, pp. 177-183. [Abstract Only, Medline].
Manca et al., "Doppler Evaluation of Left Ventricular Filling: Effect of Atenolol in Patients with Hypertension". Current Therapeutic Research, vol. 51, No. 3, 1992, pp. 334-341.
Friart et al., "Doppler evaluation of left ventricular filling: effect of verapamil on non-obstructive hypertrophic cardiomyopathy". European Heart Journal, vol. 11, No. 9, 1990, pp. 839-844.
Vanhees et al., "Influence of $\beta^1$-Versus $\beta^2$-Adrenoceptor Bloackade on Left Ventricular Function in Humans". Journal of Cardiovascular Pharmacology, vol. 8, No. 5, 1986, pp. 1086-1091.
Harrison et al., "Use of Exercise Doppler Echocardiography to Evaluate Cardiac Drugs: Effects of Propranolol and Verapamil on Aortic Blood Flow Velocity and Acceleration". Journal of the American College of Cardiology, vol. 11, No. 5, May 1988, pp. 1002-1009.
Hassager et al., "Different Effects of Calcium Antagonist and Beta-Blocker Therapy on Left-Ventricular Diastolic Function in Ischemic Heart Disease". Cardiology, vol. 96, No. 2, 2001, pp. 65-71.
Abstract in English for JP2000355577, Dec. 26, 2000.
Abstract in English for JP2004264195, Sep. 24, 2004.
Aupetit et al. "Efficacy of a beta-adrenergic receptor antagonist, propranolol, in preventing ischaemic ventricular fibrillation: dependence on heart rate and ischaemia duration". Cardiovascular Research; vol. 37, 1998, pp. 646-655.
Braunwald, E. "Control of myocardial oxygen consumption". American Journal of Cardiology, vol. 27, 1971, pp. 416-432.
Braunwald, E., "Unstable Angina: An Etiologic Approach to Management". Circulation, vol. 98, 1998, pp. 2219-2222.
Braunwald et al, ACC/AHA 2002 Guideline Update for the Management of Patients with Unstable Angina and Non-ST-Segment Elevation Myocardial Infarction-Summary Article. A Report of the American College of Cardiology/ American Heart Association Task Force on Practice Guidelines (Committee on the Management of Patients with Unstable Angina). Journal of the American College of Cardiology, vol. 40, No. 7, 2002, pp. 1366-1374.
Cannon et al., "Predictors of Non-Q-Wave Acute Myocardial Infarction in Patients With Acute Ischemic Syndromes: An Analysis from the Thrombolysis in Myocardial Ischemia (TIMI) III Trials". American Journal of Cardiology, vol. 75, May 1995, pp. 977-981.
Davies, M.J., "The birth, growth, and consequences of the atherosclerotic plaque". Dialogues in Cardiovascular Medicine vol. 4, No. 3, 1999, pp. 115-130.
Difrancesco, D. "Characterization of single pacemaker channels in cardiac sino-atrial node cells". Nature, vol. 324, 1986, pp. 470-473.
Fuster et al., "The pathogenesis of coronary artery disease and the acute coronary syndromes". The New England Journal of Medicine, vol. 326, Jan. 23, 1992, pp. 242-250 (a).
Fuster et al., "The pathogenesis of coronary artery disease and the acute coronary syndromes". The New England Journal of Medicine, vol. 326, Jan. 30, 1992, pp. 310-318 (b).
Gibbons et al., "The emerging concept of vascular remodeling". The New England Journal of Medicine, vol. 330, No. 20, 1994, pp. 1431-1438.
Givertz et al., "Clinical Aspects of Heart Failure: High-Output Failure; Pulmonary Edema". In: 16 Braunwald E, ed. Heart Disease. A textbook of cardiovascular medicine. 6th ed. Philadelphia: W.B. Saunders Company, Chapter 17, 2001, pp. 534-561.
Riesen et al., "Pharmacokinetics of oral ivabradine in healthy cats". Journal of Veterinary Pharmacology and Therapeutics, vol. 34, No. 5, Dec. 2010, pp. 469-475.
Riesen, Sabine C., "Studies on Myocardial Funny Channels and the Funny Current Inhibitor Ivabradine in Healthy Cats and Cats with Hypertrophic Cardiomyopathy". Dissertation Presented in Partial Fulfillment of the Requirements for the Degree Doctor of Philosophy

(56) References Cited

OTHER PUBLICATIONS in the Graduate School of The Ohio State University, Aug. 11, 2010, p. 1-1. http://etd.ohiolink.edu/view.dgi?acc_num=osu1281555785 [retrieved on Aug. 30, 2012].

Uechi et al., "The Effects of the Loop Diuretics Furosemide and Torasemide on Diuresis in Dogs and Cats". Journal of Veterinary Medical Science, vol. 65, 2003, pp. 1057-1061.

Val'ter, M.B., "Development of the Manufacture of Multilayer and Coated Tablets". Zhdanov Technical Equipment Plant. Translated from Khimiko-Farmatsevticheskii Zhurnal, vol. 9, No. 10, pp. 38-47, Oct. 1975, pp. 654-661.

Van Israel, Nicole, "Management of Chronic Congestive Heart Failure in Small Animals". UK VET, vol. 7, No. 2, Mar. 2002, pp. 1-7.

International Search Report and Written Opinion for PCT/EP2014052399 mailed Mar. 4, 2014.

International Search Report for PCT/EP01/04034 mailed Dec. 27, 2001.

McClellan et al., "Telmisartan". Drugs, vol. 56, No. 6, Dec. 1998, pp. 1039-1044.

The Merck Index, 11th Edition, 1989, p. 363, (referenced in Amendment filed Dec. 24, 2013 as Exhibit B).

Advanced Chemistry Development (ACD/Labs) Software V11.02 (C) 1994-2012 ACD/Labs, pp. 1-3, (referenced in Amendment filed Dec. 24, 2013 as Exhibit A).

Abstract in English for EP2127643, May 30, 2008.

International Search Report and Written Opinion for PCT/EP2012/065680 mailed on Oct. 12, 2012.

Sharma et al., "Role of Taste and Taste Masking of Bitter Drugs in Pharmaceutical Industries—An Overview". International Journal of Pharmacy and Pharmaceutical Sciences, vol. 2, Suppl. 4, Jul. 2010, pp. 14-18.

Wagner et al., "Development of disintegrating multiple-unit tablets on a high-speed rotary tablet press". European Journal of Pharmaceutics and Biopharmaceutics, vol. 50, 2000, pp. 285-291.

Granetzny et al., "Effects of a Bradycardic Agent (DK-AH 269) on Haemodynamics and Oxygen Consumption of Isolated Blood-Perfused Rabbit Hearts". Journal of Clinical and Basic Cardiology, vol. 3, No. 3, 2000, pp. 191-196.

Hansson G.K., "Inflammation, Atherosclerosis, and Coronary Artery Disease". The New England Journal of Medicine, vol. 352, 2005, pp. 1685-1695.

Ho et al. "Survival after the onset of congestive heart failure in Framingham Heart Study subjects". Circulation, vol. 88, 1993, pp. 107-115.

Katz, A.M. "Heart failure". In:Katz AM, ed. Physiology of the Heart. 3rd ed. Philadelphia: Lippincott Williams & Wilkins, 2001, pp. 658-694.

Keene et al., "Valvular heart disease". Current Veterinary Therapy VIII Small Animal Practice, Kirk, 1983, pp. 311-320.

López-Sendón et al., "Expert consensus document on beta-adrenergic receptor blockers". European Heart Journal, vol. 25, 2004, pp. 1341-1362.

Colucci et al., "Pathophysiology of Heart Failure". Braunwald E., ed. Heart Disease. A textbook of cardiovascular medicine. 6th Edition, Philadelphia, W.B. Saunders Company, vol. 1, 2001, pp. 503-533.

Chatzizisis et al., "Role of Endothelial Shear Stress in the Natural History of Coronary Atherosclerosis and Vascular Remodeling". Journal of the American College of Cardiology, vol. 49, No. 25, 2007, pp. 2379-2393.

Floras, J.S., "Clinical Aspects of Sympathetic Activation and Parasympathetic Withdrawal in Heart Failure". Journal of the American College of Cardiology, vol. 22, Supp. A, 1993, pp. 72A-84A.

Katz, A.M. Arrhythmias II: Clinical Manifestations and Principles of Therapy. In:Katz AM, ed. Physiology of the Heart. 3rd ed. Philadelphia: Lippincott Williams & Wilkins, 2001, pp. 580-629.

Janse et al., "Electrophysiological Mechanisms of Ventricular Arrhythmias Resulting from Myocardial Ischemia and Infarction". Physiological Reviews, vol. 69, No. 4, Oct. 1989, pp.1049-1169.

Colucci, W.S., "Molecular and Cellular Mechanisms of Myocardial Failure". American Journal of Cardiology, vol. 80, No. 11A, 1997, pp. 15L-25L.

Difrancesco, D. "Funny channels in the control of cardia rhythm and mode of action of selective blockers". Pharmacological Research, vol. 52, 2006, pp. 399-406.

Kedem et al., "Pacing during reperfusion elevates regional myocardial oxygen consumption". American Journal of Physiology-Heart and Circulatory Physiology, vol. 259, 1990, pp. H872-H878.

Nagatsu et al., "Bradycardia and the Role of Beta-Blockade in the Amelioration of Left Ventricular Dysfunction". Circulation, vol. 101, 2000, pp. 653-659.

Packer, M. "Therapeutic option in the management of chronic heart failure. Is there a drug of first choice?" Circulation, vol. 79, 1989, pp. 198-204.

Packer et al., "The Effect of Carvedilol on Morbidity and Mortality in Patients with Chronic Heart Failure". The New England Journal of Medicine, vol. 334, No. 21, May 23, 1996, pp. 1349-1355.

Roelandt et al., "Sudden death during longterm ambulatory monitoring". European Heart Journal, vol. 5, 1984, pp. 7-20.

Ross, R. "Atherosclerosis—An Inflammatory Disease". The New England Journal of Medicine, vol. 340, No. 2, 1999, pp. 115-126.

Sharov et al., "Evidence of Cardiocyte Apoptosis in Myocardium of Dogs with Chronic Heart Failure". American Journal of Pathology, vol. 148, No. 1, Jan. 1996, pp. 141-149.

Shizukuda et al., "Beta-Adrenergic stimulation causes cardiocyte apoptosis: influence of tachycardia and hypertrophy". American Journal of Physiology—Heart and Circulatory Physiology, vol. 275, 1998, pp. H961-H968.

Vanderlaan et al., "Site Specificity of Atherosclerosis: Site-Selective Responses to Atherosclerotic Modulators". Arteriosclerosis, Thrombosis, and Vascular Biology, vol. 24, 2004, pp. 12-22.

Waagstein, F. "Beta-Blockers in Congestive Heart Failure: the Evolutions of a New Treatment Concept—Mechanisms of Action and Clinical Implications". Journal of Clinical and Basic Cardiology, vol. 5, No. 3, 2002, pp. 215-223.

Zicha et al., "Sinus node dysfunction and hyperpolarization-activated (HCN) channel subunit remodeling in a canine heart failure model". Cardiovascular Research, vol. 66, 2005, pp. 472-481.

Wikipedia, "Heart Failure". [Retrieved from "http://en.wikipedia.org/w/index.php?title=Heart_failure&oldid=587316584" on Dec. 23, 2013.], 21 pages.

Wikipedia, "Coronary artery disease". [Accessed from http://en/wikipedia.org/w/index.php?title=Special: Book &bookcmd=download&collection_id=740d791b7d082a7c &writer=rl&return_to=Coronary+artery+disease], 2013, 9 pages.

Wikipedia, "Sinus-Tachycardia". [Accessed from http://en.wikipedia.org/w/index.php?title=Sinus_tachycardia &printable=yes on Nov. 11, 2013], 4 pages.

"Silent Ischemia and Ischemic Heart Disease". [Accessed from http://www.heart.org/HEARTORG/Conditions/HeartAttack/PreventionTreatmentofHeartAttack/Silent-Ischemia-and-Ischemic-Heart-Disease_UCM_434092_Article.jsp on Nov. 11, 2013], 2 pages.

International Search Report and Written Opinion for PCT/EP2013/076256 mailed on Feb. 7, 2014.

Furukawa et al., "Inhibition by Zatebradine, an I-f inhibitor of ventricular tachyarrhythmias in dog hearts". Japanese Journal of Pharmacology, vol. 67, Supp. 1, 1995, 68th Annual Meeting of the Japanese Pharmacological Society; Nagoya, Japan, Mar. 25-28, 1995, p. 127P.

Gupta et al., "Abstract 309: Long-Term Therapy with Ivabradine Increases ACE-2 Activity in Left Ventricular Myocardium of Dogs with Chronic Heart Failure". Basic Cardiovascular Sciences Scientific Session; New Orleans, LA, Jul. 23-26, 2012, Poster Session Three, 1 page.

Rastogi et al., "Abstract 11819: Long-Term Monotherapy with Ivabradine Attenuates Mitochondrial Permeability Transition Pore Opening in Cardiomyocytes of Dogs with Chronic Heart Failure". Scientific Sessions of the American-Heart-Association/Resuscitation Science Symposium, Orlando, FL, Nov. 12-16, 2011, 2 pages.

Amado et al., "A bradycardic agent, cilobradine, mproves left ventricular function in dogs with coronary embolization-induced

(56) References Cited

OTHER PUBLICATIONS heart failure". 77th Scientific Meeting of the American-Heart-Association; New Orleans, LA, Nov. 7-10, 2004, Abstract 2793, p. III-601.
Gomez et al., "Defective Excitation-Contraction Coupling in Experimental Cardiac Hypertrophy and Heart Failure". Science, vol. 276, May 1997, pp. 800-806.
Pogwizd et al., "Cellular Basis of Triggered Arrhythmias in Heart Failure". TCM, vol. 14, No. 2, 2004, pp. 61-66.
Belvisi et al., "Preclinical Profile of Ciclesonide, a Novel Corticosteroid for the Treatment of Asthma". The Journal of Pharmacology and Experimental Therapeutics, vol. 314, No. 2, 2005, pp. 568-574.
Couetil et al., "Inflammatory Airway Disease of Horses"., Journal of Veterinary International Medicine, vol. 21, 2007, pp. 356-361.
Dietzel et al., "Ciclesonide: An On-Site-Activated Steroid". New Drugs for Asthma, Allergy and COPD. Progress in Respiratory Research, Basel, Karger, vol. 31, 2001, pp. 91-93.
Grahnén et al., "A dose-response study comparing supression of plasma cortisol influenced by fluticasone propionate from Diskhaler and budesonide from Turbuhaler"., European Journal of Clinical Pharmacology, vol. 52, 1997, pp. 261-267.
International Search Report and Written Opinion for PCT/EP2013/077264 mailed Feb. 3, 2014.
International Search Report and Written Opinion for PCT/EP2013/077266 mailed on Feb. 11, 2014.
Kutasi et al., "Diagnostic Approaches for the Assessment of Equine Chronic Pulmonary Disorders". Journal of Equine Veterinary Science, vol. 31, 2011, pp. 400-410.
Robinson et al., "Fluticasone Propionate Aerosol is More Effective for Prevention than Treatment of Recurrent Airway Obstruction". Journal of Veterinary Internal Medicine, vol. 23, 2009, pp. 1247-1253.
"Cardiomyopathy (heart disease) in cats". International Cat Care, pp. 1-6. [Accessed at: http://www.icatcare.org/print/270 on Jun. 5, 2014].
Böhm et al., "Heart rate as a risk factor in chronic heart failure (SHIFT): the association between heart rate and outcomes in a randomised placebo-controlled trial". Lancet, vol. 376, No. 9744, Sep. 2010, pp. 886-894.
International Search Report and Written Opinion for PCT/EP2012/065704 mailed Sep. 6, 2012.
Riesen et al., "Comparison of the Effects of Ivabradine and Atenolol on Heart Rate and Echo cardiographic Variable of Left Heart Function in Healthy Cats". Journal of Veterinary Internal Medicine, vol. 25, 2011, pp. 469-476.
Riesen et al., "Effects of Ivabradine on Invasive Indices of LV Function in Anesthetized Cats with Hypertrophic Cariomyopathy". Advances in Veterinary Medicine, Book of Abstracts, Apr. 8, 2010, pp. 1-9. http://vet.osu.edu/assets/pdf/research/researchDay/2010/2010abstracts.pdf [retrieved on Aug. 30, 2012].

TASTE MASKED PHARMACEUTICAL COMPOSITION

FIELD OF THE INVENTION

The present invention relates to the manufacture of pharmaceutical compositions, especially for the preparation of formulation intermediates of active ingredients for pharmaceutical compositions.

BACKGROUND OF THE INVENTION

The manufacture of pharmaceutical compositions comprises several aspects, one of them being the task of providing active ingredients in an appropriate form. Ideally active ingredients, especially those having an unpleasant taste, are prepared so that the patient taking a pharmaceutical composition does not refrain from doing so because of the unpleasant taste.

Taste masking is useful in the field of veterinary medicine because animals are sensitive to taste, and unlike humans, cannot be "persuaded" by reasoned argument to swallow a composition that the animal perceives as unpleasant. In most cases pharmaceutical compositions for animals include specific flavors, e.g. meat flavor for predominantly carnivorous animals. Such flavors, however, simply add to the taste of the medicine itself and serve to cover the taste perception, but in many cases adding flavor is not sufficient if the taste of the compound is still perceivable by the animal patient. On the contrary, bitter or otherwise unpleasant compounds intended for oral application in veterinary medicine are preferably hidden away, especially from the animal's perception. Such taste masking is a severe restriction for the use of pharmaceutical compositions in veterinary medicine.

In addition, the release of the active ingredient of a pharmaceutical composition to the patient's body needs to be optimized with respect to the envisaged activity of the compound. This optimization applies to oral compositions, especially those that are desired to dissolve, e.g. in the stomach, shortly after administration.

The problem of an adequate formulation of an active ingredient has to be solved for every pharmaceutical composition. It occurs for all active compounds used for all sorts of medical treatments. In particular, oral dosage forms are confronted with the need of masking a taste when the addition of flavoring agents alone is not sufficient to mask the unpleasant taste of the active compound.

In pharmaceutics while developing a solid dosage form, a taste is usually masked by applying a film coat consisting of a taste neutral polymer onto a whole tablet. But this technique does not solve the problem discussed here, especially for the treatment of predominantly carnivorous animals because a film-coated tablet is usually of neutral smell which is not attractive to the animal and therefore less likely to be ingested voluntarily. Further, many animals, especially cats, have the habit of breaking down their food by biting on it several times, and thereby, destroying the masking film and releasing the unpleasant taste. Similarly, a film-covered tablet cannot be divided in parts to optimize the individual dosage without destroying the masking film. In some cases, a tablet is not the appropriate dosage form, especially when there is a necessity for precise dose adjustment that is easier by employing a liquid dosage form. Accordingly this issue also applies to liquid pharmaceutical formulations.

Metabolic disorders like diabetes can in principle be treated by the oral application of respective pharmaceutical compositions, e.g. those that comprise DPP IV-inhibitors.

Inhibitors of DPP IV belonging to the structural class of xanthine derivatives are disclosed generically by WO 02/068420 A1.

The compound 1-[(3-cyano-pyridin-2-yl)methyl]-3-methyl-7-(2-butyn-1-yl)-8-[3-(R)-amino-piperidin-1-yl]-xanthine is described explicitly in WO 2005/085246 A1, example 1(52). Its mono- and di-hydrochloride, as well as, polymorphs of the free base and the hydrochlorides are described in WO 2007/014886 A1. These applications disclose methods for the chemical synthesis of this compound along with its salts, hydrates and other forms.

International patent application PCT/EP2011/054440 pertains to pharmaceutical compositions comprising the compound 1-[(3-cyano-pyridin-2-yl)methyl]-3-methyl-7-(2-butyn-1-yl)-8-[3-(R)-amino-piperidin-1-yl]-xanthine in the form of the free base, as well as, every other chemical form, including solvates, prodrug esters, stereoisomers, and salts (especially the monohydrochloride) for the treatment of a metabolic disorder or metabolic disease of a predominantly carnivorous non-human animal like dog (canine) or cat (feline). Such disorders are selected from ketoacidosis, pre-diabetes, diabetes mellitus type 1 or type 2, insulin resistance, obesity, hyperglycemia, hyperinsulinemia, elevated blood levels of fatty acids, hyperlipidemia and/or elevated blood levels of glycerol, Syndrome X (metabolic syndrome), atherosclerosis, inflammation of the pancreas and/or inflammation of adipose tissue, preferably ketoacidosis, pre-diabetes and/or diabetes mellitus type 1 or type 2, more preferred diabetes mellitus type 2.

This application discloses an oral application of the active ingredient. However, it does not teach a specific granulation or manufacturing technique for the active compound. An appropriate taste masking of the compound is still desirable, especially because of the bitter taste of the substance.

Other examples of active ingredients intended for an oral application are those for the treatment of heart diseases. Heart diseases include for example coronary heart diseases, cardiomyopathies, cardiovascular diseases, heart failure, hypertensive heart diseases or valvular heart diseases. These different classes of heart diseases are treated with therapies or combined therapies and hence with different classes of compounds. Therapies include administering one or more ACE inhibitors, beta-blockers, angiotensine II receptor antagonists, diuretics, $Ca^{2+}$-sensitising agents, antiarrthythmic agents, cardioac glycosides or bradycardic agents such as $i_f$-channel blockers.

European patent application EP 224794 A2 discloses a number of cyclic amine derivatives falling under a general formula including their chemical synthesis, the molecule 3-[(N-(2-(3,4-dimethoxy-phenyl)-ethyl)-piperidin-3-yl)-methyl]-7,8-dimethoxy-1,3,4,5-tetrahydro-2H-3-benzazepin-2-on being one of them. They are described to exert a heart frequence lowering activity in rat. Its enationamer with the chemical name (+)-3-[(N-(2-(3,4-dimethoxy-phenyl)ethyl)-piperidin-3-(S)-yl)-methyl]-(7,8-dimethoxy-1,3,4,5-tetrahydro-2H-3-benzazepin -2-on carries the international nonproprietary name (INN) cilobradine. The derived hydrochloride can be named as cilobradine hydrochloride. Cilobradine and its hydrochloride are highly water-soluble.

WO 01/78699 A2 discloses the use of structurally diverse bradycardiac substances such as calcium channel blockers, beta-receptor blockers and $i_f$-channel blockers, optionally in combination with cardio-active substances, for treating and even inducing the regression of myocardial diseases associated with hypertrophy, in particular for treating ideopathic hypertrophic cardiomyopathies (HCM) in humans and domestic animals. One of the $i_f$-channel blockers that is mentioned is cilobradine, which has a bitter taste. WO 01/78699 A2 discloses that the active ingredient, such as cilobradine, can be provided in the form of a simple mixture with other ingredients and assembled in a capsule, in the form of a granulate or a dragée, based on the same granulate, coated with a mixture of corn starch and sugar. Solutions comprising the active ingredient dissolved in a liquid are also disclosed.

Cilobradine is further disclosed to be useful for the treatment or prevention of heart failure, by EP 1362590 A1. Whereas the examples of this publication disclose the application of the active ingredient by injection, the disclosure also describes drinking solutions which are clearly easier to handle by a patient. Another use of bradycardic substances, like $i_f$-channel blockers and especially cilobradine, is disclosed by EP 1762179 A1, which discloses that these substances can be used for improving diagnostic quality in echocardiography.

Further pharmaceutically active compounds which are advantageously applied orally and confronted with the need and/or desire of masking their taste are per se known to the skilled person.

To address the problem of taste-masking an active ingredient(s) that is incorporated into pharmaceutical compositions, specific techniques have evolved in the state of the art. These are mostly coating techniques that coat, i.e. cover, the active ingredient by another substance in which the other substance serves as a physicochemical barrier against the evaporation, dissolution, or diffusion of the active ingredient. The coated particle is used as one component of the complete pharmaceutical composition. The barrier function of the protective coating should last as long as the pharmaceutical composition is stored and/or the ingredient could otherwise be perceived by the patient. Multiphase systems can be used to keep the active ingredient in a separate phase from the remainder of the composition. However, the pharmaceutical composition should dissolve or become permeable as soon as necessary for the ingredient to become active.

One technique is to prepare particles comprising the active ingredient by using a granulation step followed by a coating step. EP 292840 A2 exemplifies this technique in its example I (¶¶ 1444-1448) where the active ingredient is mixed with starch, sugar, polyvinylpyrrolidon and magnesium stearate, and the mixture is subsequently pressed and processed into granules. These granules are then mixed with another component and pressed into tablets. Such a tablet is finally described to be coated by a mixture of sugar and talc, thus resulting in a so-called dragee (example II, ¶¶ 1449-1451).

EP 409254 A1 addresses the dissolution aspect of granular particles comprising a core and a film layer coating the core. The disclosed cores comprise the active substance and a water -swelling agent; and the film layer contains at least ethylcellulose and a substance selected from ethylcellulose, HPMC (hydroxypropylmethylcellulose), MC (methylcellulose), L-HPC (low substituted hydroxypropylcellulose) and PVP (polyvinyl pyrrolidone). The specification describes that based on the taste perception by humans it was desired to reach a masking time of at least 20 s. The disclosed coatings allowed a masking time of 1 to at 57 s.

Coatings comprised of two or more coating layers, especially double layers, are also known. For example, the U.S. Pat. No. 4,874,613 teaches coating an inert inner core containing the active substance with a first layer surrounding the core comprising a biologically inert excipient or filler (clay like kaolin or water-soluble polymer), and a second layer surrounding the first layer comprising a mixture of a cationic copolymeric acrylate resin and a basic compound (like calcium carbonate, aluminium hydroxide or magnesium carbonate). Additionally, it teaches that the active ingredient can be fixed to the core by a binder material like polyvinylpyrrolidone, methycellulose, or pharmaceutically suitable gums and that the acrylate resin for the second coating layer can be chosen from methacrylate and neutral methacrylic acid ester copolymers. This patent exemplifies a mixture of kaolin clay and povidone (polyvinyl pyrrolidone) as a first layer and a mixture of calcium carbonate and Eudragit E-100 copolymeric methacrylate resin as a second layer. In both cases isopropanol and acetone are used as solvents for the preparation of the respective coating layer and allowed to evaporate after the addition of the respective material.

WO 03/075895 A1 discloses taste masked veterinary solid compositions consisting of a substrate in pellet or tablet form in which fine-grained particles of a neutral-tasting, physiologically compatible, solid carrier material are embedded. These fine-grained particles of carrier material have an average diameter of 0.09 to 0.8 mm and are coated with an active substance. This active substance layer is covered with a protective layer of a physiologically compatible polymer matrix. Thus, the active ingredient is not present in the core but in a first layer that is protected by a second layer. In such particles, the outer layer fulfills the same task and exerts the same disadvantages as those cited above where the active substance is located in the core. The distinction is that the production process is started with an inert core and that the active ingredient is applied to that core by a coating step.

A disadvantage of layering techniques is that a highly soluble compound tends to dissolve at least partially in the coating solution during the coating step, so that after drying small amounts of the substance are then distributed also in the coating layer. In some cases this might not be critical; however, unpleasant tasting substances are perceptible by an animal which will often refrain from taking the preparation.

The technique of multiple layering can be used for the manufacture of particles with more than one active ingredient. EP 2127643 A1 discloses granules, consisting of an inert core, coated with the (first) active ingredient, further coated with a release-regulating polymer, finally coated with a so-called functional ingredient. Such functional ingredient can be, for example, an inhibitor of the first active ingredient thus allowing a timely regulated activity profile of this compound. But, the release-regulating polymer is not a polymer that completely inhibits the release of the active compound but is used as a diffusion barrier leading only to time-delayed release. Such particles do not solve the problem discussed here.

European patent application EP 551820 A1 addresses the same problem especially with respect to overall liquid medical formulations. It teaches the preparation of particles that comprise an active ingredient by fluid bed granulation processes. In a second step such granules are coated by a lacquer, also called a microencapsulation process. A large number of theoretically possible coating substances, esp. polymers, is disclosed. Exemplified substances are combinations of Eudragit® NE 30 D with HPMC, with MC and with triethyl citrate. However, the essence of this development resides in the fact that the active ingredient is not used as it is, esp. not as a water soluble salt but in its least water soluble form like the free acid or the free base. Accordingly, this teaching does not extend to the respective salts or other water soluble forms of the pharmaceutically active ingredient.

The problem of finding an appropriate taste-masking technique is also addressed by WO 2006/074185 A2, which describes dissolving or dispersing a pH dependant polymer and a so called "non-plasticizing active pharmaceutical ingredient" in a solvent which is granulated by itself (and thus forming an active ingredient containing core) or used as material for forming layers over a solid support. Both approaches are then optionally followed by applying a taste masking overcoating layer. WO 2006/074185 A2 provides that the pH dependent polymer itself serves as taste masking agent, meaning that the active compound and the protective agent are not separated in two phases but form one phase. Due to the physicochemical interaction between the compound and the polymer this one phase does not dissolve but stays intact as long as the taste perception might occur. The specification explains that useful active pharmaceutical ingredients for this technique are characterized by the fact that they are relatively non-tacky and generally will remain relatively non-tacky so as to render coated solid supports workable when combined with the first taste masking material whether or not up to about 25% by weight of a conventional anti-tack agent, such as talc or magnesium stearate is added. But, a "plasticizing" active pharmaceutical ingredient cannot meet this requirement. Accordingly this teaching cannot be generally applied to all sorts of active ingredients.

The granules (or pellets) provided by all of these techniques are usually not used per se as pharmaceutical substances but represent formulation intermediates to be integrated into more complex pharmaceutical compositions. Such a composition can be e.g. in solid form (for example a tablet), or in liquid form (for example a suspension), which is another burden for the stability and/or disintegration properties of the incorporated substance containing particles.

The scientific publication of Wagner et al. (2000), entitled "Development of disintegrating multiple-unit tablets on a high-speed rotary tablet press", in the *European Journal of Pharmaceutics and Biopharmaceutics*, volume 50, pages 285 to 291, describes the complex interplay between composition parameters such as polymers for coating, pellet size and pellet properties, the proportion of pellets in a mixture, and the type of filler-binders, and of machine parameters, such as production rate and type of feeder. The publication discloses Avicel PH 101 to be the most suitable filler-binder for the overall tablet, and with respect to coating elasticity and thickness, Eudragit FS 30 D is disclosed as an advantageous coating for granules. Pellets coated with Eudragit FS 30 D are taught to withstand the stress of tableting. However, they show disadvantages with respect to the disintegration process of the tablet.

To date, taste masking of pharmaceutically active ingredients which are water-soluble, especially highly water-soluble ones that also contain either at least one basic group and/or a bitter taste, is not resolved.

Due to the basic group and/or the bitter taste such compounds have to be masked away from the smell and/or taste perception of the patient. But the water soluble nature of the compound regularly leads to at least traces of the compound diffused within the particle and/or the coatings layers already during the coating process itself, i.e. before the respective coating layer has dried, just because the compound is dissolved at least partially by the solvent of the respective coating layer material during the coating process. Accordingly, whereas the main portion of the compound might be hidden away by the established coating techniques, traces of it may be perceptible. Such perception by the patient, especially animals, may result in the patent refraining from taking the medicament or composition.

For example, published application US 2005/287211 A1 discloses particles comprising a core of microcrystalline cellulose spheres coated by the three layers: a substance layer, a middle layer and an outer coating layer. Middle layers of the disclosed examples comprise povidone or hydroxypropylmethylcellulose (HPMC) as sole polymers. The disclosed outer coating layers comprise e.g. a mixture of HPMC and ethylcellulose or a poly(meth)acrylate. However, all exemplified middle layers additionally comprise a strongly water soluble ionic compound, in most cases $NaH_2PO_4$, $Na_2HPO_4$, $Na_2CO_3$ or citrate. This strongly water soluble ionic compound influences the physicochemical properties of the coatings not only during the dissolution of the particle (as addressed by the respective publication) but also during the production of the particle, which leads to perceptible amounts of the active ingredient by the patient/animal.

WO 2009/011967 A1 discloses particles that comprise a core of sucrose coated by the layers of a substance layer (a non-steroidal anti-inflammatory drug), a first protective layer comprising HPMC or a mixture of HPMC and polyethlenglycol (PEG), an optional enteric coating layer or intermediate coating layer (a methacrylate/acrylate-polymer with triethylcitrate) and an optional second protective layer comprising HPMC again (e.g. a mixture of HPMC and PEG). Additionally, one of the coating layers comprises a strongly water soluble ionic compound. Taste and taste masking are not addressed or considered in WO 2009/011967 A1.

WO 2010/007515 A2 discloses particles comprising an active substance containing core, protected by an inner layer (polymers which swell or dissolve in the GI tract, e.g. a mixture of HPMC and PEG), an intermediate layer with a specific physiological activity (a protease-inhibitor and/or absorption enhancer, embedded in PEG as a binding polymer), an outer layer (polymers which swell or dissolve in the GI tract like the ones for the inner layer), and optionally, a further outer layer with a gastro-resistant polymer (methacryl-copolymers or cellulose acetate-phthalate). These particles are optimized, especially by the application of a protease-inhibitor and/or absorption enhancer and the selection of polymers, to resist untimely dissolution in the GI tract and to provide a programmable release of the active ingredient(s). The aspect of influencing the dissolution process and/or the activity of the drug substance by the addition of specifically acting proteins is not addressed by WO 2010/007515 A2.

WO 2008/075372 A1 discloses particles comprising a core of a starch containing sugar sphere, covered by a seal coat, then a substance layer (drug and HPMC) as a second coat and an outer layer comprising a mixture of the material Surelease® (ethylcellulose admixed with coconut oil) mixed in a ratio of 6:1 (w/w) with HPMC. But, these particles do not comprise a further protective layer. It was also found disadvantageous to store the active substance in a middle layer and not in the lowest possible layer. This structure affects the dissolution profile, as well as, the production process.

Finally, the particles of WO 2008/027993 A2 are composed of an inert core, an amorphous layer containing the drug (with a crystallization inhibiting polymer, also named solubility-enhancing polymer, and a solubility enhancing organic acid), a protective seal-coating layer (povidone) and finally a "lag-time coating" (TPR coating; water-insoluble polymer and an enteric polymer). All examples disclose outer coatings with the plasticizers diethylphthalate or triethylcitrate. So, this specific architecture aims at a sustained release following lag-time but is not optimized with respect to the production of the particle.

Accordingly, there is a need in the art to optimize the palatability of pharmaceutical compositions, especially for use in veterinary medicine by masking the taste of a pharmaceutically active compound which is water-soluble, especially a highly water-soluble active compound that also comprises either at least one basic group and/or a bitter taste. Such compositions should at the same time allow the release of the ingredient in the patient's body as soon as necessary.

Exemplary preferred pharmaceutical compositions include the pharmaceutically active ingredients of DPP IV-inhibitors, $i_f$-channel blockers, phosphodiesterase III inhibitors, cyclooxygenase 2 inhibitors, and benzodiazepine receptor agonist.

Ideally, a masking technique would allow acceptable formulation intermediates to be incorporated into oral dosage forms for pharmaceutical compositions, especially in the field of veterinary medicine in the case of an unpleasant taste of the active ingredient. Such a masking technique should be applicable to a substance containing particles that contain the active ingredient(s) in the inner core, as well as, to granules that provide the active ingredient in the form of a coating layer over an inert or already sub-coated core, the layer(s) beneath and/or the core optionally comprising other active ingredients.

A desired masking technique should be especially useful for those pharmaceutically active ingredients that are highly soluble in water and/or in other solvents that are used for coating layers. Ideally, the desired masking technique should be applicable to solid and non-solid, especially liquid, formulations with only minor variations. The dosage form should also allow subdividing into pieces or volumetric dispensing in order to adapt the dose, without destroying the taste masking of the pharmaceutically active ingredient.

Preferably, the desired masking technique is highly flexible with respect to the amount of the pharmaceutically active ingredient to be incorporated into the pharmaceutical composition; cost effective; and easy to apply in a standard manufacturing apparatus.

SUMMARY OF THE INVENTION

This problem is solved by the invention of a taste masked multi-layered particle comprising a pharmaceutically active ingredient, comprising:
a) an inert core,
b) one or more coating layer(s) comprising the pharmaceutically active ingredient and a binder,
c) an intermediate coating layer (seal coating) free from a low molecular weight water -soluble ionic compound, comprising a water-soluble pharmaceutical film-forming compound, selected from
   (i) hydroxypropyl methylcellulose (HPMC) and polyethylene glycol (PEG) or
   (ii) poly(1-vinylpyrrolidin-2-one) (PVP); and
d) an outer coating layer (final or taste masking coating) free from a low molecular weight water-soluble ionic compound, comprising
   (i) a poly(meth)acrylate or
   (ii) a mixture comprising 60-90% (w/w) ethylcellulose (EC) and 10-40% (w/w) hydroxypropyl methylcellulose (HPMC),
wherein the pharmaceutically active ingredient is water-soluble and comprises either at least one basic group and/or a bitter taste.

In other words: The solution of the above mentioned problems consists in well-assembled coated drug loaded subunits (multi-layered particles or pellets). According to the invention they can be produced starting from inert particles (or spherical carriers or pellets) that are coated stepwise by specific layers. For this purpose they are first layered once or more than once with a layer comprising a specific pharmaceutically active ingredient; the drug layer is then covered by an intermediate coating layer (seal coating) and then by an outer coating layer (final or taste masking coating).

A second aspect of the present invention provides methods for the production of such multi-layered particles.

A further aspect of the present invention provides the use of certain compounds or mixtures of compounds for the assembly of intermediate coating layers (seal coating) or of outer coating layers (final or taste masking coating) of such multi-layered particles.

Further aspects of the present invention provide uses of the multi-layered particles according to the invention as well as pharmaceutical uses and pharmaceutical compositions comprising them.

These and other aspects of the present invention are described herein by reference to the following figures and examples. The figures and examples serve for demonstrative purposes and do not limit the scope of the claims.

As explained below in more detail and demonstrated by the examples of this application, the multi-layered particles according to the invention are taste masked and at the same time they show advantageous dissolution profiles. Especially the exemplified material basic butylated methacrylate copolymer turned out to be an extremely good outer coating layer which is insoluble in neutral pH environments (meal and mouth of the patient), but dissolves quickly at acidic pH (stomach), thereby allowing the particle to disintegrate and to release the drug. They further provide an acceptable mouth-feeling, i.e. no grittiness for the patient.

Accordingly, the multi-layered architecture of the particles of the invention allows the formulation of palatable pharmaceutical compositions, especially for use in veterinary medicine, even with pharmaceutically active ingredients that would otherwise be rejected by taste-sensitive patients. Thus the acceptance and compliance of respective pharmaceutical composition is ameliorated.

The features, esp. the mechanical stability of the multi-layered particles according to the invention further allow versatile pharmaceutical compositions with the possibility for accurate dose adjustment, in solid as well as in overall liquid or pasteous form.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE PRESENT INVENTION

Figure 1A:
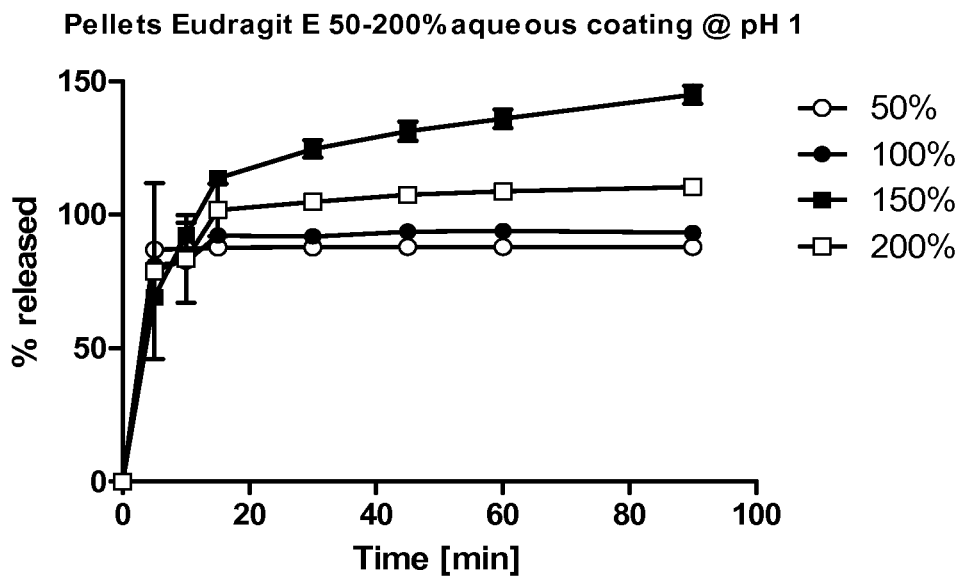
FIG. 1: Dissolution curves at pH 1 (FIG. 1A) and pH 6.8 (FIG. 1B) from multi-layered particle prototypes coated with basic butylated methacrylate copolymer, produced according to Example 1, at different coating levels (aqueous process). (Means±SD, n≥3, are shown).

The invention provides taste masked multi-layered particles.

Herein and in the appended claims, the singular forms "a", "an", and "the" include plural reference unless the context clearly dictates otherwise. Thus, for example, reference to "a preparation" includes a plurality of such preparations. Unless defined otherwise, all technical and scientific terms used herein have the same meaning as is commonly understood by one of skill in the art to which this invention belongs at the time of filing. The meaning and scope of terms should be clear; however, in the event of any latent ambiguity, definitions provided herein take precedent over any dictionary or extrinsic definition. Herein, the use of "or" means "and/or" unless stated otherwise. Furthermore, the use of the term "including", as well as other forms such as "includes" and "included" is not limiting. All given ranges and values may vary by 1 to 5% unless indicated otherwise or known otherwise by the person skilled in the art, therefore, the term "about" was omitted from the description. Although any methods and materials similar or equivalent to those described herein can be used in the practice or testing of the present invention, the preferred methods, devices, and materials are now described.

"Particles", according to the invention, are overall solid pieces produced for example by the processes described below; the word "Pellet" can be used synonymously for "particle". They are regularly used as formulation intermediates esp. for pharmaceutical compositions, meaning that they provide the pharmaceutically active ingredient in a form that can be incorporated in finally composed pharmaceutical compositions. These can be overall solid preparations of material, e.g. solid pharmaceutical compositions; alternatively, the particles according to the invention can make up the solid phase of a suspension in an overall non-solid, e.g. pasteous or especially liquid composition, esp. a pharmaceutical liquid composition.

The particles according to the invention are "multi-layered" which means that they are characterized by a well-designed architecture in which inert particles (or spherical carriers or pellets) are coated by one or more layers comprising a specific pharmaceutically active ingredient, on top of this by an intermediate coating layer (seal coating) and then by an outer coating layer (final or taste masking coating). Details of this architecture as well as materials that can be used for it are explained below.

"Taste masked", in the sense of the invention, means that molecules with an unpleasant taste are hidden away from the patient's perception, not only covered with another, more pleasant taste or flavor. "Taste masked" according to the invention is to be understood as a functional term, especially with respect to the natural taste perception of a human or an animal. The task of masking the taste of a pharmaceutically active ingredient is regarded to be solved as soon as a statistically significant number (more than 60%, preferably more than 70%, even more preferred more than 80%, most preferred more than 90% or even more than 95%) of the addressed patient population does not refrain from voluntary ingestion of a pharmaceutical composition comprising the respective taste masked multi-layered particles in comparison to a pharmaceutical composition comprising a less efficiently masked or non-masked preparation of the same pharmaceutically active ingredient in an overall comparable pharmaceutical composition.

The taste masked multi-layered particles according to the invention can be used for pharmaceutical compositions for the medical treatment of humans as well as for the medical treatment of animals. Such medical treatment means all kinds of treatments that can be exerted by oral administration of a pharmaceutically active compound, including prophylaxis, immunization and therapy.

The multi-layered particles according to the invention are especially suitable and intended for use in veterinary medicine. This feature of the invention is not to be understood as a restriction of the patient population to animals only. It is to be understood as a quality feature. Animals like e.g. cats are characterized by an extremely good perception of taste in comparison to humans, and the examples provided with this application show that the preferred solutions do solve the problem even with respect to cats as addressed patient population. Multi-layered particles are especially covered by the invention, when the masking of the taste is so efficient that even taste sensitive animals like cats or dogs as patient population specifically addressed by the derived, fully formulated pharmaceutical composition (at the mentioned predefined percentage) do not refrain from the voluntary ingestion of the derived, fully formulated pharmaceutical composition.

The use of multi-layered particles according to the invention for use in veterinary medicine is preferred because the need for taste masking of pharmaceutically active ingredients is especially persistent in this technical area. This is especially true in the context of the compound groups described in more detail below that are specifically addressed by the invention.

"Pharmaceutically active ingredients", in the sense of the invention, are per se all kinds of chemical or biological substances useful for the prophylaxis, immunization or therapy of a disease of an animal or a human patient. The pharmaceutically active ingredient is regularly incorporated in its chemical form most appropriate for the medical treatment, e.g. as solvate, salt or ester. Preferred examples of pharmaceutically active ingredients will be explained below.

Form a chemical point of view, the pharmaceutically active ingredients relevant for the invention are "water-soluble and comprise either at least one basic group and/or a bitter taste".

As explained above, the invention had to be made with respect to such compounds that have a high tendency to (i) be perceived by the patients and (ii) to dissolve in the coating material during the storage of the particles and/or the derived formulation and/or in the solution of the coating material during the production of the particles. As exemplified, the coatings according to the invention allow such a highly sophisticated taste masking.

Water-solubility is in most cases due to polar groups as part of the compound allowing water molecules to assemble respectively and to build up a hydration shell. Most preferred are ionic compounds which quantitatively dissolve in at least one anion and at least one cation during the solvation in water.

Preferred are compounds with a bitter taste because especially this taste has to be masked and can be masked by the teaching of the invention. For example several N-containing groups are polar or even cationic and at the same time responsible for a bitter taste.

The essence of the invention resides in the unique architecture of the multi-layered particles, comprising an inert core and the coating layers described in the following.

The "inert core" according to the invention is a particle (or spherical carrier or pellet). It has been found advantageous to use particles with a diameter of about 50 to 300 μm, preferably with a small degree of variation. Preferred sub-ranges are defined below.

The material used for the inert core is chemically inert, in the sense that it does not react with any of the other ingredients of the multi-layered particle according to the invention and especially does not interfere with the intended pharmacological mechanism exerted by the pharmaceutically active ingredient of the multi-layered particle. Examples for a material used for the inert core are cellulose, esp. microcrystalline cellulose, starch, lactose, sugar, mannitol or mixtures thereof.

The coating process as described below regularly starts with the material for the inert cores. According to the invention it is intended that each single particle of this starting material serves as a single core for each multi-layered particle according to the invention. The process is a statistical process with Gauss' distribution curves for the results of each step. This leads to statistical results, meaning that each layer has got an average thickness. It is preferred that multi-layered particles with more than only one single inert core particle be sieved off and in doing so be excluded from incorporation into a pharmaceutical composition.

The methods for the coating process, i.e. for the subsequent addition of layers onto a smaller particle are per se known to the person skilled in the art. Such are described for example in the textbook "Developing Solid Oral Dosage Forms—Pharmaceutical Theory and Practice", chapter 34, edited by Yihong Qiu, Yisheng Chen and Geoff G. Z. Zhang; Elsevier (2009).

Also the apparatus for granulation processes are known to the person skilled in the art, for example "Developing Solid Oral Dosage Forms—Pharmaceutical Theory and Practice", chapter 34, edited by Yihong Qiu, Yisheng Chen and Geoff G. Z. Zhang; Elsevier (2009).

The "one or more coating layer(s) comprising the pharmaceutically active ingredient and a binder" which, according to the invention, is layered onto the core particle, contains the pharmaceutically active ingredient, regularly in its chemical form appropriate for the medical treatment. It further contains a binder and optionally other ingredients that as a mixture are intended to form the respective coating layer.

Useful binder materials include but are not limited to tragacanth, gelatin, starch, cellulose materials such as methyl cellulose, microcrystalline cellulose and sodium carboxy methyl cellulose, alginic acids and salts thereof, polyethylene glycol, PVP, guar gum, polysaccharide acids, sugars, invert sugars and the like. Preferred are hydroxypropyl methylcellulose (HPMC) and/or polyvinylpyrrolidone (PVP).

The material HPMC (also called Hypromellose; the name HPMC according to DIN EN ISO 1043-1: 2002-06, E 464) is a mixed ether of cellulose with 2-hydroxypropyl and methyl groups. Technically it is usually prepared by the reaction of cellulose with methylchloride and propylene oxide. It can be purchased commercially, e.g. by the supplier Harke Pharma under the trade name Pharmacoat®.

The material PVP (also called Poly(1-vinylpyrrolidin-2-one) or Polyvidon; the name PVP according to DIN EN ISO 1043-1: 2002-06) is a vinylpolymer of the general structural formula:

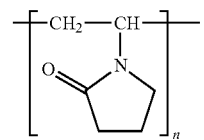

and with molecular weights between 2,500 and 750,000 g/mol, which again depends on the degree of polymerization. They are characterized by K values which are calculated from the viscosity of 1% or 5% aqueous solution. PVPs are technically usually prepared by radical polymerization of 1-vinylpyrrolidin-2-one.

Binders may be used in an amount of up to 60% (w/w). It has been found advantageous that the drug layer on the pellets consists of up to 40% (w/w), preferably 5 to 20% (w/w) of binder. More preferred ranges are defined below. In another preferred aspect according to the invention the drug layer on the pellets consists of 1-30% (w/w) of the binder.

The coating material for this layer can advantageously be applied in the form of a liquid solution or suspension of the binder material in water which is allowed to evaporate after the addition of the material.

While using the fluid bed coating process, it is preferred to spray the liquid mixture onto the core particles. It is preferred that the coating layer comprising the pharmaceutically active ingredient and a binder is added up to a thickness of more than 20 μm, and increasingly preferred more than 30, 40, 50, 60, 70, 80 and 100 μm and mostly preferred between 50 and 100 μm. Such variability allows adding the pharmaceutically active ingredient to an extent that is appropriate to reach the desired concentration of active ingredient in the finally prepared pharmaceutical composition.

This coating step can be repeated in order to allow the addition of a second coating layer(s) comprising the pharmaceutically active ingredient. The material for this optional second layer can be identical with the first one. However, variations of this composition in order to optimize physicochemical parameters also lie well within the ambit of the invention. The second layer can be added to the same or to a different thickness than the first layer. In doing so a double coating layer comprising the pharmaceutically active ingredient of more than 200 μm in total is possible. Example 1 of this specification shows the production of a particle comprising two layers each comprising the pharmaceutically active ingredient and a binder with a thickness of about 140 μm in total.

The "intermediate coating layer (seal coating) comprising a water-soluble pharmaceutical film-forming compound" is to be understood as a complete coating layer around/on top of the layer comprising the pharmaceutically active ingredient serving especially two purposes: (i) mechanical stability for the particle as a whole and especially for the integrity of the layer comprising the pharmaceutically active ingredient, and (ii) barrier against the dissolution of the pharmaceutically active ingredient within the particle, especially during the production of the particle as well as during the storage period of the complete multi-layered particles and the fully formulated pharmaceutical composition. Besides the water-soluble pharmaceutical film-forming compound, further ingredients can optionally be present in this coating layer.

According to the invention, this coating layer is layered onto the one or more coating layer(s) comprising the pharmaceutically active ingredient and a binder. It has been found advantageous to apply this coating layer by way of suspension or solution in water or an organic solvent, also mixtures of water and e.g. ethanol are possible.

Appropriate water-soluble film-forming compounds are those that qualify as pharmaceutically acceptable chemical compounds. From a chemical perspective they can be described as hydrophilic polymers or mixtures thereof. According to the invention, such a water-soluble pharmaceutical film-forming compound is especially selected from (i) a mixture of hydroxypropyl methylcellulose (HPMC) and polyethylene glycol (PEG) or (ii) poly(1-vinylpyrrolidin-2-one) (PVP). According to another aspect of the invention the water-soluble pharmaceutical film-forming compound is selected from for example HPMC, PVP, methyl cellulose, hydroxy ethyl methyl cellulose, hydroxy ethyl cellulose or sodium carboxymethyl cellulose or mixture of one or more of these compounds.

The material hydroxypropyl methylcellulose (HPMC) has already been discussed above.

The material polyethylene glycol (PEG) makes up a large group of polyethers with the general structural formula:

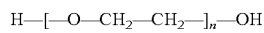

$$H-[-O-CH_2-CH_2-]_n-OH$$

and with molecular weights between 200 and 5,000,000 g/mol, which depends on the degree of polymerization. Technically they are usually prepared by anionic polymerization of oxiran (ethyleneoxid) or polycondensation of 2-chloroethanol (ethylene chlorohydrin). Depending on the chain length, they comprise a liquid to waxy overall appearance. They dissolve in water and several organic solvents. According to the invention it is preferred to use a PEG with a molecular weight between 4,000 and 8,000 preferably around 6,000 g/mol which are usually called PEG 4000, PEG 8000 and PEG 6000 and the like, the name depending on the molecular weight. Such PEG can be purchased commercially, e.g. by the supplier Dow Chemicals, Schwalbach, Germany, under the trade name Carbowax Sentry®.

In a preferred mode of the invention the material for this coating layer additionally comprises talc and/or magnesium stearate. In another aspect of the invention this coating additionally layer comprises one or more of the following anti-tacking agents such as talc, magnesium stearate, calcium docosanoate, stearic acid, calcium arachinate, hydrogenated castor oil, or triglycerides.

The mixture for this coating layer can advantageously be added to the respective particles in the form of an aqueous solution or suspension. Employing an aqueous process is especially advantageous with respect to cost, work safety and environmental reasons.

The material poly(1-vinylpyrrolidin-2-one) (PVP) has already been presented above.

According to the invention it is preferred to add PVP and optionally talc in the form of a solution in an organic solvent like ethanol and/or aceton.

The thickness of the seal coating layer (c) can vary with respect to the specific particle. Preferably, it lies between 5 and 40% (w/w) of the drug layered particles, more preferred between 10 and 30% (w/w) even more preferred between 15 and 25% (w/w).

The ideal thickness in each case can be developed experimentally by a person skilled in the art, with respect to the following considerations: The seal coating serves as protective coating to mechanically stabilize the complete particle and the pharmaceutically active ingredient containing layer for the following coating steps and to prevent migration of the drug active ingredient into the outer layer when the final coating is applied or even during storage (see above). The seal coating is deemed to be thick enough when no (or only traces of) the compound can be detected on the outer surface of the particles. An appropriate detection method is Energy Dispersive X-ray analysis (EDS). The final decision, however, is based on the statistical analysis of the derived, fully formulated pharmaceutical composition with the envisaged taste sensitive patient population, as explained above.

The "outer coating layer (final or taste masking coating) comprising (i) a poly(meth)acrylate or (ii) a mixture comprising 60-90% (w/w) ethylcellulose (EC) and 10-40% (w/w) HPMC" is a complete coating layer around/on top of the intermediate coating layer (seal coating). Without wishing to be bound by this theory, it is believed that especially this coating is responsible for the taste masking properties of the multi-layered particles according to the invention, esp. by inhibiting the diffusion of the pharmaceutically active ingredient to the surface of the particle, neither during production nor during the storage of the particles and/or the derived pharmaceutical compositions. It further serves the purpose of mechanical stabilization of the particle as a whole and especially for the integrity of the layers underneath.

The material poly(meth)acrylate appropriate for the invention is a polymer derived from the polymerisation of esters of acrylic and methacrylic acid.

The state of the art discloses a broad range of chemical derivatives of such a polymer, derived by the addition of certain side chains (R) to the backbone, i.e. by the polymerization with different methacrylic acid esters, e.g. with neutral ester groups ($-COOCH_3$ or $-COOC_4H_9$), anionic groups ($-COOH$), cationic groups ($-COOCH_2CH_2N(CH_3)_2$) and neutral ionic groups ($-COOCH_2CH_2N^+(CH_3)_3Cl^-$).

The use of poly(meth)acrylates with neutral or cationic groups is preferred.

This material can be purchased in different physical forms like aqueous dispersion, organic solution, granules or powders. With respect to the mode of application it is preferred to use a powder or a solution that fits to the solvent to be used for the respective coating process, respectively.

Further physico-chemical properties of this material can be found in the literature, e.g. in the Eudragit® Application Guidelines, Evonik Röhm GmbH, Business Line Pharma Polymers, Darmstadt, Germany, which company is also one commercial supplier of this material.

The representatives of this material which are useful for the invention, are characterized by their specific solubility profile that depends on the pH value of the surrounding medium and is preferably insoluble in neutral pH environments but soluble at acidic pH values. Such useful representatives are for example:

A cationic copolymer based on dimethylaminoethyl methacrylate, butyl methacrylate, and methyl methacrylate with a ratio of 2:1:1, preferably with a molecular weight between 40,000 and 50,000, more preferred about 47,000 g/mol (or basic butylated methacrylate copolymer, as disclosed in European Pharmacopoeia or the INCI name dimethylaminoethyl methacrylate copolymer, or the IUPAC name poly(butyl methacylate-co-(2-dimethyl-aminoethyl) methacrylate-co-methyl methacrylate) 1:2:1); commercially available e.g. under the trade name Eudragit® E, or Eudragit® E PO in its powder form, from Evonik Röhm GmbH, Business Line Pharma Polymers, Darmstadt, Germany.

A copolymer of ethyl acrylate, methyl methacrylate and a low content of a methacrylic acid ester with quaternary ammonium groups (trimethylammonioethyl methacrylate chloride) with a ratio of approx. 1:2:0.1, preferably with a molecular weight between 30,000 and 40,000, more preferred about 32,000 g/mol (or Ammonio Methacrylate Copolymer, Type B, as disclosed in European Pharmacopoeia); commercially available e.g. under the trade name Eudragit® RS, or Eudragit® RS PO in its powder form, from Evonik Röhm GmbH.

A copolymer of ethyl acrylate, methyl methacrylate and a low content of a methacrylic acid ester with quaternary ammonium groups (trimethylammonioethyl methacrylate chloride) with a ratio of approx. 1:2:0.2, preferably with a molecular weight between 30,000 and 40,000, more preferred about 32,000 g/mol (or Ammonio Methacrylate Copolymer, Type A, as disclosed in European Pharmacopoeia); commercially available e.g. under the trade name Eudragit® RL, or Eudragit® RL PO in its powder form, from Evonik Röhm GmbH.

A neutral copolymer based on ethyl acrylate and methyl methacrylate, ratio approx. 2:1, preferably with a molecular weight of at least 500,000, more preferred between 700,000 and 800,000, most preferred about 750,000 g/mol (or Polyacrylate Dispersion 30 Per Cent, as disclosed in European Pharmacopoeia); commercially available e.g. under the trade name Eudragit® NE in 30% dispersion from Evonik Röhm GmbH.

In one mode of the invention the poly(meth)acrylate component is blended with magnesium stearate which is especially useful when an organic solvent process is used for the application of this coating onto the respective particles. Without wishing to be bound by this theory, it can be assumed that these two compounds in this combination fulfill these functions: poly(meth)acrylate acts as functional coating, allowing especially a pH dependent disintegration of the particle (stable in neutral pH, disintegrating in acidic pH); magnesium stearate functions as anti-tacking agent. Talc and/or colloidal silica can optionally be added to counteract electrostatic charging. In another aspect of the invention other anti-tacking agents are for example talc, magnesium stearate, calcium docosanoate, stearic acid, calcium arachinate, hydrogenated castor oil, or triglycerides.

In an alternative approach the poly(meth)acrylate coating can be applied by an aqueous process. In this case it is preferred to form a total mixture comprising sodium lauryl sulfate (as wetting and dispersing agent), stearic acid (as salt former and further for forming a colloidal solution with poly (meth)acrylate) and/or magnesium stearate (as anti-tacking agent). Alternative anti-tacking agents are for example talc and/or silica. Again, the given functions of these additional components are based on the best knowledge up to date but cannot be binding with respect to the disclosure of the invention. Talc and/or colloidal silica can optionally further be added to counteract electrostatic charging.

Alternatively, a mixture comprising 60-90% (w/w) ethylcellulose (EC) and 10-40% (w/w) HPMC can be used as material for the outer coating layer.

The material ethylcellulose (EC; the name according to DIN EN ISO 1043-1: 2002-06) is the ether of cellulose with ethyl groups. Technically it is usually prepared by the reaction of alkalicellulose with ethylchloride, which can lead to types of EC differing with respect to the degree of substitution. Ethylcelluloses with substitution degrees between about 1.1 and 1.4 are soluble in water; those with higher degrees of substitution are soluble in organic solvents. Commercially available EC types with substitution degrees between about 2.2 and 2.6 are thermoplastic with a softening point between around 150 and 160° C. Commercially available EC types are offered with different molecular weights which further influence the physico-chemical properties of the material like their viscosity.

According to the invention it is preferred to use EC with a substitution degree between 2.2 and 2.6 and/or with a degree of polymerization resulting in a viscosity of 41-49 mPa·s (measured as 5% solution in 80% toluene and 20% ethanol). Such EC can be purchased commercially, e.g. by the supplier Dow Chemical under the trade name Ethocel® Std. 45.

The material HPMC has already been presented above.

According to the invention, the ratio of HPMC and EC can be varied in the given frame in order to achieve the desired release profile, esp. with respect to the following considerations. Without wishing to be bound by this theory it is assumed that in a blend of EC and HPMC according to the invention, the HPMC dissolves firstly after ingestion by the patient and thus leaves pores in the EC film. Then water can penetrate through the pores into the core of the pellets and thereby allow the pharmaceutically active ingredient to be released with a lag time, i.e. the time the HPMC needs to be washed out of the film. The EC/HPMC film composition and the coating thickness (see below) can be optimized in a way to generate a lag time that is considered long enough to allow the dosage form to be ingested without the drug being released.

For both alternatives, the poly(meth)acrylate and the EC/HPMC films, the coating thickness and the way the coating is applied to the pellets can be varied/optimized in order to achieve the desired drug release profile or make the process feasible, i.e. aqueous vs. organic solvent spraying process. Such variations lie well within the reach of a person skilled in the art. Preferred values are disclosed in more detail below.

Moreover, the final coating layer may advantageously comprise further substances. For example magnesium stearate is used to counteract electrostatic charging during processing. Another example is siliciumdioxide to reduce electrostatic charging of the product. Further examples are talc, magnesium stearate, calcium docosanoate, stearic acid, calcium arachinate, hydrogenated castor oil, or triglycerides.

Both, the intermediate coating layer (seal coating) (c) and the outer coating layer (final or taste masking coating) (d) are further characterized by the feature "free from a low molecular weight water-soluble ionic compound".

Without wishing to be bound by this theory, this feature has been found to be one important reason for the efficiency of the taste-masking of the particle as well as of the derived pharmaceutical compositions and thus the usefulness of the invention. Whereas the state of the art teaches that compounds like $NaH_2PO_4$, $Na_2HPO_4$, $Na_2CO_3$ or citrates, especially the salts of strong acids with strong bases, are useful as dissolution aids of the particles and thus helpful for the application of the pharmaceutical ingredient to the patient's body. However, in the context of the taste-masking of a pharmaceutically active ingredient which is water-soluble and comprises either at least one basic group and/or a bitter taste, it was found to be advantageous to avoid such compounds.

However, less ionic compounds like talc, stearic acid, sodium lauryl sulfate or magnesium staerate, especially oxides or the salts of weak acids used e.g. as lubricants, coloring agents and/or anti-tacking agents and the like are found to be not so critical for the taste-masking effect and are thus allowed as optional ingredients. This aspect will be explained in more detail below.

The selection of such additional compounds in the layers (c) and (d) is thus limited by their ability to dissolve in water. They are uncritical and therefore not water-soluble ionic compounds in the sense of the application as long as 1 g of such a compound is completely dissolved by not less than 100 ml water, at a temperature of 25° C. and 1013.25 hPa atmospheric pressure. Increasingly preferred they possess solubility values of at least 250, 500, 750, 1000, 2000, 3000, 4000, 5000, 6000, 7000, 8000, 9000, 10000, 15000 and more than 20000 ml water for the total dissolution of 1 g of the respective substance under the same conditions.

Compounds with low molecular weight, according to the invention, are defined as those with a molecular weight below 750 Da, increasingly preferred below 700, 600, 500, 400, 300, 200 and 150 Da.

The different coating materials are preferably applied to the respective particles in the form of a liquid solution or suspension in an appropriate solvent. This solvent can be selected from (purified) water or organic solvents.

One preferred mode of the invention is a taste masked multi-layered particle according to the invention described above, wherein the pharmaceutically active ingredient is selected from one or more of the following compound groups:
α) a DPP IV inhibitor,
β) an $i_f$-channel blocker,
γ) a phosphodiesterase III inhibitor,
δ) a cyclooxygenase 2 inhibitor and/or
ε) a benzodiazepine receptor agonist.

These compound groups are a priori not defined by their chemical classes, but they are defined by their high specificity for one or (theoretically) more than one of these five specific targets, which specificity is high enough to allow a medical therapy based on the interaction of these compounds with their specifically bound targets. The binding characteristics of the compounds to their specific targets reside in interactions of the compounds with the three dimensional structure of the addressed region of the target protein, mainly based on ionic interactions, hydrogen bonds, Van-der-Waals bonds and/or hydrophilic/hydrophobic interactions in general. Accordingly, all compounds within one of these groups are to be seen as a group with similar stereochemistry and a similar architecture of hydrophilic/hydrophobic, ionic etc. groups placed on the scaffold of the compound.

This correlates with the fact that the invention has proven to be especially useful for pharmaceutically active ingredients that tend to dissolve and/or to diffuse in water or any other solvent, especially in a solvent that is used for the addition of coating materials onto respective particles.

Among these substances, the invention is useful for those with an unpleasant, e.g. bitter taste. Such a taste is regularly due to specific ionic groups on the respective compound, which in the other hand are necessary for the specific interaction with the target to exert the medical effect.

"DPP IV inhibitors" according to the invention are those chemical compounds that interact with and inhibit the enzyme dipeptidyl peptidase IV (DPP IV). It is believed that the inhibition of DPP IV decreases the GLP-1 proteolysis and thus prolongs the half-life of endogenous full-length (active) GLP-1 and in doing so leads to increased plasma levels of glucagon like peptide 1 (GLP-1). As a consequence, GLP-1 induces the secretion of insulin from pancreatic β-cells in a glucose dependent manner. A reduction of glucagon levels as well as an enhancement of long-term pancreatic β-cell function in vivo are potentially additional beneficial features of GLP-1 elevation. Especially the enhancement of long-term pancreatic β-cell function can be characterized as a disease modifying effect; GLP-1 agonism preserves β-cell mass by increased proliferation and decreased apoptosis which effects can be characterized as a β-cell regeneration effect. Further effects of GLP-1 elevation according to the invention include slowing of gastric motility and induction of satiety.

In conclusion, DPP IV inhibitors can be used for the therapy of metabolic disorders or metabolic diseases like ketoacidosis, pre-diabetes, diabetes mellitus type 1 or type 2, insulin resistance, obesity, hyperglycemia, hyperinsulinemia, elevated blood levels of fatty acids, hyperlipidemia and/or elevated blood levels of glycerol, Syndrome X (metabolic syndrome), atherosclerosis, inflammation of the pancreas and/or inflammation of adipose tissue, especially the treatment of diabetes mellitus type 1 or type 2, even more preferred diabetes mellitus type 2.

Useful compounds are disclosed in WO 2005/085246 A1, especially in the derived Patent EP 1758905 B1.

The experimental part of the application comprises one example of a compound for the treatment of a metabolic disease, esp. of diabetes type 2 by a bitter tasting DPP IV inhibitor from the xanthine class, i.e. by 1-[(3-cyano-pyridin-2-yl)methyl]-3-methyl-7-(2-butyn-1-yl)-8-[3-(R)-amino-piperidin-1-yl]-xanthine monohydrochloride, which is especially preferred in this context.

Such multi-layered particles can be used for the treatment of metabolic disorders, esp. of diabetes type 2, e.g. by incorporation into a respective medical formulation.

"$i_f$-channel blockers" according to the invention are those chemical compounds that interact with and inhibit the $i_f$-channel. They are believed to be useful for treating and even inducing the regression of myocardial diseases associated with hypertrophy, in particular for treating ideopathic hypertrophic cardiomyopathies (HCM) in humans and domestic animals.

Useful compounds are disclosed by EP 065229 B1, especially zatebradine (see below), and U.S. Pat. No. 3,708,485, especially alinidine (see below).

Very useful and preferred compounds are disclosed in EP 224794 B1, among which there is the preferred $i_f$-channel blocker is (+)-3-[(N-(2-(3,4-dimethoxy-phenyl)ethyl)-piperidin-3-(S)-yl)-methyl]-(7,8-dimethoxy-1,3,4,5-tetrahydro-2H-3-benzazepin-2-on which is also useful for the treatment or prevention of heart failure. It has been given the international nonproprietary name (INN) cilobradine. The hydrochloride form is called cilobradine hydrochloride.

The experimental part of the application comprises one example for the taste masking of a compound for the treatment of heart disease from this compound group; this is one representative of the chemical class of cyclic amine derivatives, i.e. of bitter tasting cilobradine (or of the respective hydrochloride form). Especially in this taste masked form it can be used for human and for animal therapy, e.g. by incorporation into a respective medical formulation for the treatment of heart diseases.

"Phosphodiesterase III inhibitors" according to the invention are those chemical compounds that interact with and inhibit the enzyme phosphodiesterase III (PDE 3). Without wishing to be bound by this theory, the inhibition of PDE 3 is thought to cause peripheral vasodilation which results in decreased pressure, translating into smaller cardiac preload and afterload and thus decreases the failing heart's workload.

Useful compounds are disclosed by WO 2005/084647 A1 and especially the derived patent EP 008391 B1.

One prominent example of such compounds is (RS)-6-[2-(4-methoxyphenyl)-1H-benzimidazol-5-yl]-5-methyl-4,5-dihydropyridazin-3(2H)-one, also known under the INN pimobendan and described e.g. in EP 008391 B1 and WO 2005/084647 A1. Pimobendan is known and usable as cardiotonic, hypotensive and anti-thrombotic compound and also functions as a positive inotrope which sensitizes and increases the binding efficiency of cardiac myofibril to the calcium ions that are already present without increasing the consumption of oxygen and energy. According to the invention this activity is also ascribed to the molecules named phosphodiesterase III inhibitors.

Especially in a taste masked form according to the invention, phosphodiesterase III inhibitors, especially pimobendan can be used for human and for animal therapy, e.g. by incorporation into a respective medical formulation for the treatment of the diseases mentioned above, especially heart diseases, especially of congestive heart failure.

"Cyclooxygenase 2 inhibitors" according to the invention are those chemical compounds that interact with and inhibit the enzyme cyclooxygenase 2 (COX-2), especially those that inhibit COX-2 selectively over COX-1. Cyclooxygenase is the enzyme responsible for converting arachidonic acid into prostaglandin H2, which is the first step in the synthesis of prostaglandins, which are mediators of inflammation. Without wishing to be bound by this theory, it is believed that this specific inhibition leads to an anti-inflammatory effect, accompanied with analgesic and fever reducer effects.

Useful compounds are disclosed by EP 002482 B1. One prominent example of these compounds is 4-hydroxy-2-methyl-N-(5-methyl-2-thiazolyl)-2H-1,2-benzothiazine-3-carboxamide-1,1-dioxide, also known under the INN meloxicam, which is non-steroidal chemical compound.

Especially in a taste masked form according to the invention, cyclooxygenase 2 inhibitors, especially meloxicam can be used for human and for animal therapy, e.g. by incorporation into a respective medical formulation for the treatment of inflammatory diseases, including inflammation associated with osteoarthritis, or (other) rheumatic diseases, as an analgetic and/or as fever reducer.

"Benzodiazepine receptor agonists" according to the invention are those chemical compounds that interact with and bind to the benzodiazepine receptor, especially without subtype selectivity. Without wishing to be bound by this theory it is believed, that especially low affinity partial agonists of the benzodiazepine receptor without subtype selectivity are effective for the treatment of epilepsy, especially of idiopathic epilepsy and/or of behavior abnormalities, especially anxiety.

Several appropriate compounds are disclosed in WO 97/09314 A1 and WO 2005/004867 A2, for example the compound 1-(4-chlorophenyl)-4-piperidinoimidazolin-2-one. A preferred compound useful for this purpose is 1-(4-chlorophenyl)-4-(4-morpholinyl)-2,5-dihydro-1H-imidazol-2-one, disclosed in WO 2004/032938 A1, which has been given the INN imepitoin.

Especially in a taste masked form according to the invention, benzodiazepine receptor agonists, especially imepitoin can be used for human and for animal therapy, e.g. by incorporation into a respective medical formulation for the treatment of central nervous system disorders, esp. epilepsy, idiopathic epilepsy and/or anxiety.

The pharmaceutically active ingredient is regularly incorporated in its chemical form most appropriate for the medical treatment, e.g. as solvate, salt or ester. Especially the salt forms, and among the these the forms of the respective hydrochlorides are mostly preferred for the exemplified molecules of 1-[(3-cyano-pyridin-2-yl)methyl]-3-methyl-7-(2-butyn-1-yl)-8-[3-(R)-amino-piperidin-1-yl]-xanthine, and the monohydrochloride respectively (representative of DPP IV inhibitors) and (+)-3-[(N-(2-(3,4-dimethoxy-phenyl)ethyl)-piperidin-3-(S)-yl)-methyl]-(7,8-dimethoxy-1,3,4,5-tetrahydro-2H-3-benzazepin-2-on and/or the respective hydrochloride (representative of $i_f$-channel blockers).

One preferred mode of the invention is a taste masked multi-layered particle according to the invention described above, further comprising one or more additional layers between the inert core and/or between one of the coating layers (b) to (d) and/or on top of coating layer (d).

Such additional layers can be coating layers in the sense of this application, i.e. making up a complete coat or closed film around the particles underneath, or just a layer of additional material between or on top of the other coating layers.

For example one of the coating layers disclosed herein can be applied more than once and thus make up a subject of this aspect of the invention. Further, e.g. protective layers might be concluded from the state of the art.

In an alternative, a material is added that does not form a closed film but still exerts positive effects. These materials can for example be anti-tacking agents that ameliorate the further processing of the respective particulate material. Such anti-tacking agents are per se known for the skilled person. They can for example further consist of pigments, and/or flavors which advantageously be added on top of the outer coating layer (final or taste masking coating). Also such materials are per se known for the skilled person.

One preferred mode of the invention is a taste masked multi-layered particle according to the invention, wherein the material for the inert core is cellulose, preferably microcrystalline cellulose.

As explained above, the chemically inert material used for the inert core can be selected from different materials. A preferred material is cellulose, especially microcrystalline cellulose. Especially this material has turned out to be useful, with respect to the further processing of the material, but also with respect to the physical properties of the finally formulated multi-layered particles. Especially microcrystalline cellulose gives the finally formulated multi-layered particles such a degree of flexibility that they can be incorporated in e.g. tablet formulations without destroying them during the compressing step of the tableting process.

Particles of microcrystalline cellulose can be purchased e.g. under the trade name Cellets® 100 from the company Syntapharm (Harke Group), Mülheim, Germany.

In another preferred aspect the inert core particles of the are preferably selected from a pharmaceutically acceptable material which upon contact with water shows a minimal or negligible swelling. Preferable materials are selected from lactose, carbohydrates, sugar alcohols, such as mannitol, sorbitol, maltitol, glucose, non-pareil-seeds, calcium phosphate, cellulose, preferably microcrystalline cellulose (MCC), and starch, and mixtures thereof, more preferably lactose, most preferably agglomerated α-lactose-monohydrate [Ph.Eur./USP-NF/JP] with a particle size $d_{50}$ of ca. 180 μm.

Lactose such as agglomerated lactose, with the characteristics described above, is also suitable for use in the core because of its particle size, non-hygroscopicity, and the fact that it at least partly undergoes plastic deformation upon compression so that the core will not break into pieces in the tablet press.

One preferred mode of the invention is a taste masked multi-layered particle according to the invention, wherein the binder for coating layer (b) comprising the pharmaceutically active ingredient is selected from HPMC and PVP or a mixture thereof and optionally additional ingredients, preferably the HPMC Hypromellose, USP Substitution Type 2910 (apparent viscosity 4.8-7.2 mPas) and/or PVP K30 and optionally additional ingredients.

Such materials have already been described above. A preferred material for this coating layer (HPMC Hypromellose, USP Substitution Type 2910; apparent viscosity 4.8-7.2 mPas) is commercially available under the trade name Pharmacoat® 606, sold by Harke Pharma GmbH, Mülheim, Germany.

Alternatively preferred is the material PVP K30 with a molecular weight between 44 and 54 kg/mol. Such PVP can be purchased commercially, e.g. by the supplier BASF, Ludwigshafen, Germany, under the trade name Kollidon® 30.

One preferred mode of the invention is a taste masked multi-layered particle according to the invention, wherein coating layer (b) comprises 80 to 95% (w/w), preferably 82.5 to 90% (w/w), more preferred 84.5 to 87.5% (w/w) of the pharmaceutically active ingredient, and 5 to 20% (w/w), preferably 10 to 17.5% (w/w), more preferred 12.5 to 15.5% (w/w) of the binder.

Especially this ratio has turned out to be advantageous for the physical characteristics of the material during its application, on the one hand, and the stability and flexibility of the finally coated particle during storage and/or tableting. Variations within these frames are accessible for a person skilled in the art.

One other not less preferred mode of the invention is a taste masked multi-layered particle according to the invention, wherein coating layer (b) comprises 60 to 70% (w/w) of the pharmaceutically active ingredient, 25 to 35% (w/w) of HPMC as binder and 0.5-3% (w/w) magnesium stearate.

Especially in this context magnesium stearate is an advantageous lubricant with a positive influence especially on the coating process. This is documented by the examples. An appropriate magnesium stearate is for example Parteck® LUB MST, sold by the commercial provider Merck KGaA, Darmstadt, Germany.

One preferred mode of the invention is a taste masked multi-layered particle according to the invention, wherein the intermediate coating layer (seal coating) (c) additionally comprises talc, preferably 10 to 30% (w/w) talc, more preferred 15 to 25% (w/w) % talc, most preferred 21-23% (w/w) talc.

In another preferred aspect of the invention the said intermediate coating layer (seal coating) (c) additionally comprises preferably 5 to 30% (w/w) talc.

This is applicable to both alternatives of the seal coating that are comprised by the invention.

One preferred mode of the invention is a taste masked multi-layered particle according to the invention, wherein the material for the intermediate coating layer (seal coating) (c), (i), HPMC and PEG, is selected from the HPMC Hypromellose, USP Substitution Type 2910 (apparent viscosity 2.4-3.6 mPas) and/or PEG 6000.

Especially this material has turned out to be useful for the process itself as well as for the mechanical stability and flexibility of the derived particles. A representative for such a HPMC is commercially available under the trade name Pharmacoat® 603, sold by Harke Pharma GmbH, Mülheim, Germany. The material PEG has already been explained above.

One preferred mode of the invention is a taste masked multi-layered particle according to the invention, wherein the material for the intermediate coating layer (seal coating) (c), (i) comprises 65 to 75% (w/w) HPMC, 7.5 to 12.5% (w/w) PEG 6000 and 19 to 23% (w/w) talc.

Especially this mixture has proven to be useful as documented by example 1.

In another preferred aspect of the invention the said intermediate coating layer (seal coating) (c) preferably 60 to 90% (w/w) HPMC, 1 to 1-15% (w/w) PEG 6000 and 9 to 25% (w/w) talc.

One preferred mode of the invention is a taste masked multi-layered particle according to the invention wherein the material for the intermediate coating layer (seal coating) (c), (ii) PVP, is selected from PVP K 30.

Both of these materials have been presented above. Especially this mixture has proven to be useful as documented by example 2.

One preferred mode of the invention is a taste masked multi-layered particle according to the invention, wherein the material for the intermediate coating layer (seal coating) (c), (ii), comprises 70-80% (w/w) PVP and 20-25% (w/w) talc.

Especially this mixture has proven to be useful as documented by example 2.

In another preferred aspect said intermediate coating layer (seal coating) (c), (ii), comprises 70-95% (w/w) PVP and 5-30% (w/w) talc.

One preferred mode of the invention is a taste masked multi-layered particle according to the invention, wherein the material for the outer coating layer (final or taste masking coating) (d) (i), poly(meth)acrylate, is a basic butylated methacrylate copolymer.

As explained above, several representatives of the polymer class of poly(meth)acrylates can be used as integral part of the outer coating layer of multi-layered particles according to the invention. However, especially the basic butylated methacrylate copolymer has proven to exert the intended solubility profile, i.e. a high stability around a neutral pH value and the tendency to solve at an acidic pH. This is documented by example 1, especially by the measurements that are documented by FIGS. 1 to 3, i.e. for the fully formulated multi-layered particles as well as for a fully composed tablet comprising such particles.

As said above, this polymer can be characterized as a cationic copolymer based on dimethylaminoethyl methacrylate, butyl methacrylate, and methyl methacrylate with a ratio of 2:1:1, preferably with a molecular weight between 40,000 and 50,000, more preferred about 47,000 g/mol. It is preferably used in its powder form for the suspension to be applied in building up the coating layer.

Such a material is commercially available, e.g. under the trade name Eudragit® E, or Eudragit® E PO in its powder form, from Evonik Röhm GmbH, Business Line Pharma Polymers, Darmstadt, Germany.

In line with the explanations above and as exemplified especially by example 1 of this specification, the following modes of this aspect of the invention are preferred because of the advantageous properties of the derived particles with respect to stability, flexibility, usefulness during the coating process and last but not least the solubility profile in combination with the effective taste masking: Taste masked multi-layered particles according to the invention, wherein the material for the outer coating layer (final or taste masking coating) (d) (i)

comprises 50-80% (w/w) poly(meth)acrylate, 0-8% (w/w) sodium lauryl sulfate, 0-35% (w/w) stearic acid and/or 0-35% (w/w) magnesium stearate;

comprises poly(meth)acrylate and stearic acid in a weight ratio of 80:20 to 60:40, more preferred 75:25 to 65:35, most preferred 70:30; and/or makes up a coating level of at least 50% (w/w) (based on the weight of the particles beneath this coating), preferably 100 to 300% (w/w), more preferred 150 to 250% (w/w), even more preferred 180 to 220% (w/w), most preferred 190 to 210% (w/w).

Especially the advantageous role of the thickness of this final coating layer, based on poly(meth)acrylate, is documented by example 1.

One preferred mode of the invention is a taste masked multi-layered particle according to the invention wherein the material for the outer coating layer (final or taste masking coating) (d) (ii), is selected from EC with a viscosity range of 41-49 mPas (measured as 5% solution in a mixture of 80% toluene and 20% ethanol and an ethoxyl content of 48.0-49.5%) and/or HPMC with a methoxyl content of 28-30%, a hydroxypropyl content of 7-12% and a viscosity range of 4-6 mPas (measured as 2% solution in water).

The usefulness of this alternative taste masking coating with these selected materials has been proven by example 2 of this specification.

An appropriate EC (ethylcellulose) for is for example the product Ethocel® 45 cps STD Premium, sold by the commercial provider Dow Chemicals, Schwalbach, Germany. An appropriate magnesium stearate for this taste masking coating is for example Parteck® LUB MST, sold by the commercial provider Merck KGaA, Darmstadt, Germany.

One preferred mode of the invention is a taste masked multi-layered particle according to the invention wherein the material for the outer coating layer (final or taste masking coating) (d) (ii), comprises 50-75% (w/w) EC, 15-40% (w/w) HPMC and 0-25% (w/w) magnesium stearate, preferably 50-60% (w/w) EC, 20-25% (w/w) HPMC and 17.5-22.5% (w/w) magnesium stearate.

Examples for such coatings are given in following table 1, along with preferred suspensions for the application of such material, i.e. by spraying onto the respective not covered particles (so called "SC pellets" according to Example 1) employing a fluid bed based process. Alternative experimental settings are equally preferred. Each compound is further explained to exert special physicochemical functions; these are assumptions up to the best knowledge at the time being but not intended to limit the scope of the protection.

TABLE 1

Composition of EC/HPMC/magnesium stearate film coat (aqueous and organic solvent process), as alternative taste and/or odor masking coating

| Solvent process | | Component | Function of respective component | Amount of respective component [% (w/w)] |
|---|---|---|---|---|
| 1 | aqueous (EC/HPMC 60:40) | EC | functional coating | ca. 52.2 |
| | | HPMC | pore former | ca. 34.8 |
| | | Magnesium stearate | anti-tacking agent, reduction of electrostatic charging | ca. 13 |
| 2 | aqueous (EC/HPMC 80:20) | EC | functional coating | ca. 69.6 |
| | | HPMC | pore former | ca. 17.4 |
| | | Magnesium stearate | anti-tacking agent, reduction of electrostatic charging | ca. 13 |
| 3 | organic (EC/HPMC 60:40) | EC | functional coating | ca. 52.2 |
| | | HPMC | pore former | ca. 34.8 |
| | | Magnesium stearate | anti-tacking agent, reduction of electrostatic charging | ca. 13 |
| 4 | organic (EC/HPMC 80:20) | EC | functional coating | ca. 69.6 |
| | | HPMC | pore former | ca. 17.4 |
| | | Magnesium stearate | anti-tacking agent, reduction of electrostatic charging | ca. 13 |

A preferred mode of this aspect of the invention is made up by taste masked multi-layered particles according to this aspect, wherein the material for the outer coating layer (final or taste masking coating) (d) (ii) makes up a coating level of at least 25% (w/w) (based on the weight of the particles beneath this coating), preferably 25 to 100% (w/w), more preferred 50 to 90% (w/w), even more preferred 70 to 80% (w/w), most preferred 72.5 to 77.5% (w/w).

Representatives with these values are described in example 2.

One preferred mode of this aspect of the invention is a taste masked multi-layered particle according to the invention, wherein the outer coating layer (final or taste masking coating) (d) of the particle is characterized in mode (i) (poly(meth)acrylate) by a thickness of 50 to 150 µm, preferably 60 to 140 µm, more preferred 70 to 130 µm, even more preferred 75 to 125 µm, most preferred 77 to 119 µm, or in mode (ii) (mixture comprising EC and HPMC) by a thickness of 10 to 150 µm, preferably 12 to 120 µm, more preferred 15 to 100 µm, most preferred 20 to 50 µm. All of these values are to be understood with a variance of ±10 µm.

As described in example 1 for outer coatings of mode (i) (poly(meth)acrylate) such an outer coating is obtainable by a final coating step using an aqueous coating solution and a coating level of 200% with a variance of ±10 µm. Such particles show an advantageous taste-masking effect accompanied with an advantageous dissolution profile and are therefore preferred embodiments. Variations of the process, esp. the use of an organic solvent and/or different coating levels can be applied by a person skilled in the art in order to reach the other named values of thickness of the respective outer coating layers (final or taste masking coating) (d) (i) and (ii), respectively. Such particles are equally preferred.

As said above, multi-layered particles according to the invention can comprise additional layers that can be coating layers in the sense of this application, i.e. making up a complete coat or closed film around the particles underneath, or just a complete or incomplete layer of additional material between or on top of the other coating layers.

One preferred mode of this aspect of the invention pertains to taste masked multi-layered particles according to the invention, wherein the one or more additional layers between the inert core and/or between one of the coating layers (b) to (d) and/or on top of coating layer (d) comprise(s) colloidal siliciumdioxide (silica), preferably 0.1-5% (w/w) (based on the weight of the final particles), more preferred 0.2-2.5% (w/w), most preferred 0.2-1% (w/w).

As exemplified by example 2, it has been found advantageous to add such material on top of the particles during the production process after drying of one coat and before the addition of the next coat, especially as anti-tacking agent.

One preferred mode of this aspect of the invention pertains to taste masked multi-layered particles according to the invention, wherein an additional coating layer(s) is a final outer-coating on top of coating layer (final or taste masking coating) (d) and the material for this additional coating layer (s) is selected from HPMC with a methoxyl content of 28-30%, a hydroxypropylcontent of 7-12% and a viscosity range of 4-6 mPas (measured as 2% solution in water).

This has been found very advantageous for multi-layered particles that are intended for the incorporation into overall liquid formulations, esp. oily liquid pharmaceutical compositions. The additional layer serves two purposes: (i) a mechanical protection against the other particles in the suspension and (ii) an additional protection against water that might tend to diffuse through the oily suspension into the particles.

One preferred mode of the invention is a taste masked multi-layered particle according to the invention wherein one or more of the layer material(s) comprise(s) additional substances, preferably filler substances, binders, wetting agents, glidants, lubricants, dispersing agents, coloring agents and/or anti-tacking agents, selected from one or more of: mannitol, starch, talc, titaniumdioxide, sodium lauryl sulfate, sodium dodecylsulfate, stearic acid, magnesium stearate, silica and medium chain triglycerides.

In addition, preferred taste masked multi-layered particles according to the invention are those, wherein one or more of the layer material(s), preferably for one of the seal coating and/or final coating comprise(s) additional substances selected from flavoring agents, pigments and substances for the reduction of electrostatic charging, more preferred meat flavor, pigments and/or siliciumdioxide.

For example, it has been found advantageous to choose an anti-tacking agent, preferably magnesium stearate, e.g. magnesium stearate ParTeck® LUB MST, commercially available, e.g. by the supplier Merck KGaA, Darmstadt, Germany, as an additional ingredient for coating layer (b). The optionally incorporated anti-tacking material can advantageously be added in the form of a suspension in a solvent, e.g. suspended in the solution/suspension used for the adding of the respective coating layer during the respective coating step. Alternatively it can be added in the form of a powder onto the dried particles after the respective layer is built up and dried.

In another/additional preferred mode of the invention the material for the intermediate coating layer (seal coating) (c) additionally comprises talc and/or magnesium stearate.

For the outer coating layer it has been found advantageous when the applied poly(meth)acrylate component is blended with magnesium stearate as anti-tacking agent, which combination is especially useful when an organic solvent process is used for the application of this coating onto the respective particles. Talc and/or colloidal silica (siliciumdioxide) can optionally be added to counteract electrostatic charging.

In the alternative approach when the poly(meth)acrylate coating is applied by an aqueous process, it is preferred to form a total mixture comprising sodium lauryl sulfate (as wetting and dispersing agent), stearic acid (as salt former and further for forming a colloidal solution with poly(meth)acrylate) and/or magnesium stearate (as anti-tacking agent). Alternative anti-tacking agents are for example talc and/or silica. Talc and/or colloidal silica can optionally further be added to counteract electrostatic charging.

Coloring agents may include but are not limited to titanium dioxide, and dyes suitable for food and natural coloring agents such as grape skin extract, beet red powder, beta-carotene, annato, carmine, turmeric, paprika, etc. The amount of coloring agent used may range from about 0.05 to about 3.5%(w/w) of the total dosage form.

However, as discussed above, the feature "free from a low molecular weight water-soluble ionic compound" is limiting. The selection of such compounds is limited by their ability to dissolve in water, as explained above.

Further, not less preferred embodiments of the invention pertain to taste masked multi-layered particles according to the invention, wherein:
the inert core is characterized by a diameter of 50 to 300 µm, preferably 75 to 250 µm, more preferred 100 to 200 µm;
wherein the final coated particle is characterized by an overall diameter of 80 to 800 µm, preferably 90 to 600 µm, more preferred 100 to 400 µm; and/or
wherein the pharmaceutically active ingredient in its incorporated chemical form makes up 1 to 50% (w/w) of the final multi-layered particle, preferably 2 to 25% (w/w), more preferred 3 to 22.5% (w/w) and most preferred 5 to 20% (w/w).

One preferred mode of the invention is a taste masked multi-layered particle according to the invention wherein the pharmaceutically active ingredient (a) (a DPP IV inhibitor) is selected from 1-[(3-cyano-pyridin-2-yl)methyl]-3-methyl-7-(2-butyn-1-yl)-8-[3-(R)-amino-piperidin-1-yl]-xanthine or any appropriate form and/or salt thereof, preferably 1-[(3-cyano-pyridin-2-yl)methyl]-3-methyl-7-(2-butyn-1-yl)-8-[3-(R)-amino-piperidin-1-yl]-xanthine monohydrochloride.

This compound has been found to be an appropriate compound for the treatment of metabolic diseases via the addressed target DPP IV. On the other hand it is water-soluble, especially in its salt form, and is characterized by a bitter taste that tends to be rejected especially by animal patients. Accordingly, there was a need to taste mask this compound. As documented by example 1, the invention disclosed here allows an effective taste masking of this compound so that it can be applied for a wide range of patients now.

One preferred mode of the invention is a taste masked multi-layered particle according to the invention comprising 1-[(3-cyano-pyridin-2-yl)methyl]-3-methyl-7-(2-butyn-1-yl)-8-[3-(R)-amino-piperidin-1-yl]-xanthine monohydrochloride as pharmaceutically active ingredient, comprising:
a) an inert core comprising microcrystalline cellulose,
b) two coating layer(s) each of them comprising 60 to 90% (w/w) of the pharmaceutically active ingredient and 10 to 40% (w/w) of HPMC as binder,
c) an intermediate coating layer (seal coating) comprising 65 to 75% (w/w) HPMC, 7.5 to 12.5% (w/w) PEG 6000 and 19 to 23% (w/w) talc and
d) an outer coating layer (final or taste masking coating) comprising 50-80% (w/w) basic butylated methacrylate copolymer, 5-8% (w/w) sodium lauryl sulfate, 8-35% (w/w) stearic acid and 18-26% (w/w) magnesium stearate,
wherein the material for the outer coating layer (d) (final or taste masking coating) makes up a coating level of 190 to 210% (w/w).

Such a multi-layered particle as well as a method for its production are demonstrated by example 1. The process described there is summarized in the flow chart of table 2.

As can be seen in table 2, the layering of the pharmaceutically active ingredient can be divided into two steps. Regardless of the identity of the compound, this is generally preferred when a high drug load has to be achieved. This might especially be due to technical reasons, i.e. to technical parameters of the fluid bed apparatus, as each employed fluid bed process equipment has a certain minimum/maximum loading capacity. Each process therefore can only be operated until a certain point before the maximum loading capacity is reached. For example in case of 1-[(3-cyano-pyridin-2-yl)methyl]-3-methyl-7-(2-butyn-1-yl)-8-[3-(R)-amino-piperidin-1-yl]-xanthine monohydrochloride the maximum loading capacity is reached when the mass of the material has increased to approx. 300% based on the amount that was originally employed, i.e. has reached 3 times the weight of the starting material.

It might also be possible and with no significant effect for the product quality to split each processed material into two or more sub-batches that are further processed separately. For example the pellets produced in the first coating step (so called IR1 pellets, according to example 1) can be split into sub-batches which are again layered with drug until a several-fold (in this case three-fold) mass increase is reached. The two or more sub-batches are then mixed and further processed together, or again split into sub-batches, depending on the scale of equipment that is selected for the next coating steps.

As further demonstrated by example 1, it is possible to apply the seal coating byway of an aqueous process. Despite the risk that the drug migrates into the outer layers of the seal coating during the process, the finally resulting multi-layered particles turned out to be useful for the treatment of cats which did not refrain from ingesting the derived pharmaceutical form.

Example 1 discloses a multi-layered particle comprising 1-[(3-cyano-pyridin-2-yl)methyl]-3-methyl-7-(2-butyn-1-yl)-8-[3-(R)-amino-piperidin-1-yl]-xanthine monohydrochloride with a taste masking coating based on basic butylated methacrylate copolymer, comprising 62.5% (w/w) basic butylated methacrylate copolymer (Eudragit® E PO), 6.2% (w/w) sodium lauryl sulfate, 9.3% (w/w) stearic acid and 21.9% (w/w) magnesium stearate, added in aqueous solution, to a total amount of around 200% solid deposit (percentage based on the amount of "SC pellets" starting material).

It was surprising to find that even with this highly water soluble active substance, all drug layering and polymer coating steps could be performed using aqueous as well as organic solvent coating processes without the bitter active ingredient migrating up to a critical extent into the outer polymer layers. This was proven by SEM coupled with x-ray/EDS (Energy Dispersive X-ray analysis).

The total composition of final taste masked multi-layered particles according to the invention comprising 1-[(3-cyano-pyridin-2-yl)methyl]-3-methyl-7-(2-butyn-1-yl)-8-[3-(R)-amino-piperidin-1-yl]-xanthine monohydrochloride as active ingredient, produced by the outlined steps 1 to 4 of example 1, is given in table 5. It represents a preferred aspect of the invention. Certain functions that can most probably be ascribed to the respective components have also been listed there; however, this does in no way limit the scope of the invention.

The data of example 1 reveal that multi-layered particles coated with basic butylated methacrylate copolymer exhibit an increasingly delayed release at pH 6.8, depending on the coating thickness, and an immediate release at pH 1. Accordingly, they are able to mask effectively the taste of a pharmaceutically active ingredient in the oral cavity (pH 6.8) while facilitating immediate drug release in the stomach (pH 1).

Especially particles coated with basic butylated methacrylate copolymer at a coating level of about 200% and/or a thickness of 77 to 119 μm of the outer coating layer (d) show the desired drug release profile, irrespective of the solvent used in the coating process.

A preferred aspect of this aspect is a taste masked multi-layered particle as described before, wherein the pharmaceutically active ingredient in its incorporated chemical form makes up 5 to 25% (w/w) of the final multi-layered particle (calculated as free base), preferably 10 to 23% (w/w), more preferred 18 to 22% (w/w), most preferred 20 to 21% (w/w).

Such values have turned out to be useful with respect to the potency of the compound, on the one hand, and the need to design pharmaceutical compositions with favorable concentrations of the active ingredient.

One preferred mode of the invention is a taste masked multi-layered particle according to the invention wherein the pharmaceutically active ingredient ((3) (an $i_f$-channel blocker) is selected from zatebradine (1-(7,8-dimethoxy-1,3,4,5-tetrahydro-2H-3-benzazepin-2-on-3-yl)-3-[N-methyl-N-[(2-(3,4-dimethoxyphenyl)ethyl]amino]-propane), 3-[(N-(2-(3,4-dimethoxy-phenyl)-ethyl)piperidin-3-yl)-methyl]-(7,8-dimethoxy-1,3,4,5-tetrahydro-2H-3-benzazepin-2-on, its enantiomer cilobradine ((+)-3-[(N-(2-(3,4-dimethoxy-phenyl)ethyl)-piperidin-3-(S)-yl)-methyl]-(7,8-dimethoxy-1,3,4,5-tetrahydro-2H-3-benzazepin-2-on) or alinidine (2-(N-allyl-2,6-dichloro-anilino)-2-imidazoline), mostly preferred cilobradine hydrochloride ((+)-3-[(N-(2-(3,4-dimethoxy-phenyl)ethyl)-piperidin-3-(S)-yl)-methyl]-(7,8-dimethoxy-1,3,4,5-tetrahydro-2H-3-benzazepin-2-on hydrochloride).

These compounds, especially cilobradine and cilobradine hydrochloride, have been found to be appropriate compounds for the treatment of heart diseases, especially for the treatment of heart failure, via the addressed target, the $i_f$-channel. On the other hand it is water-soluble, especially in its salt form, and has got a bitter taste that tends to be rejected especially by animal patients. Accordingly, there was a need to taste mask this compound. As documented by example 2, the invention disclosed here allows an effective taste masking of this compound, accompanied by a useful dissolution profile in the patient's mouth or intestine, so that it can be applied for a wide range of patients now.

One preferred mode of the invention is a taste masked multi-layered particle according to the invention comprising cilobradine hydrochloride as pharmaceutically active ingredient comprising:
a) an inert core comprising microcrystalline cellulose,
b) one coating layer comprising 60 to 70% (w/w) of the pharmaceutically active ingredient, 25 to 35% (w/w) of HPMC as binder and 0.5-3% (w/w) magnesium stearate,
c) an intermediate coating layer (seal coating) comprising 70-80% (w/w) PVP K 30, 20-25% (w/w) talc and 0.5-5% (w/w) siliciumdioxide and
d) an outer coating layer (final or taste masking coating) comprising a mixture comprising 50-60% (w/w) EC, 20-25% (w/w) HPMC, 17.5-22.5% (w/w) magnesium stearate and 0.5-3% (w/w) siliciumdioxide,
wherein the material for the outer coating layer (d) (final or taste masking coating) makes up a coating level of 72.5 to 77.5% (w/w).

Such a multi-layered particle as well as a method for its production are demonstrated by example 2. The process described there is summarized in the flow chart of table 10.

Like described before, the coating may generally be applied by an aqueous or an organic solvent spraying process, which can be optimized experimentally. In the case of this compound it was found to be preferable to add the coating layer comprising the pharmaceutically active ingredient by ways of an aqueous solution and the next two layers by ways of an organic solution, the solvent for the intermediate coating step being a mixture of 94.4% (v/v) acetone and 5.6% (v/v) ethanol, the solvent for the final coating step composed of a 1:1 mixture (v/v) of methanol and dichloromethane, due to the high solubility of the drug in water.

The thickness of the outer coating layer (final or taste masking coating) may be varied between e.g. 50-300% solid deposit (percentage based on the initial amount of the respective SC pellets as defined in the cited example), in order to achieve the desired dissolution behaviour. In this example, it was found to be sufficient to apply the final coating to a thickness of about 75% based on the initial amount of SC pellets (result of step 2) employed in the process.

According to the dissolution data collected in example 2, the dissolution from EC/HPMC coated pellets is delayed, therefore providing efficient taste and/or odor masking of the bitter active ingredient cilobradine hydrochloride. This could be verified by acceptance tests with laboratory cats.

Usually, EC/HPMC films show a sustained release behavior more or less independent of pH. In this case, however, the product surprisingly showed a slower release at pH 6.8 which is favorable with regards to the invention, i.e. providing efficient taste masking in the oral cavity and a faster release in the acidic stomach. Without wishing to be bound by this theory, this may be explained by the lipophilicity profile of the specific pharmaceutically active ingredient, which is slightly more lipophilic at neutral pH values than at acidic pH values. This, together with the coating applied, is expected to result in a slower release at neutral pH values, sufficient to use the respective multi-layered particles for the application of this drug for the treatment of patients, esp. of animals like cats.

A preferred mode of this aspect is a taste masked multi-layered particle as described before, wherein the pharmaceutically active ingredient in its incorporated chemical form makes up 2 to 10% (w/w) of the final multi-layered particle (calculated as hydrochloride), preferably, 3 to 7.5% (w/w), more preferred 4 to 6% (w/w), most preferred 5.25 to 5.75% (w/w).

Such values have turned out to be useful with respect to the potency of the pharmaceutically active ingredient, on the one hand, and the need to design pharmaceutical compositions with favorable concentrations of the active ingredient.

One preferred mode of the invention is a taste masked multi-layered particle according to the invention wherein the pharmaceutically active ingredient ($\gamma$) (a phosphodiesterase III inhibitor) is pimobendan ((RS)-6-[2-(4-methoxyphenyl)-1H-benzimidazol-5-yl]-5-methyl-4,5-dihydropyridazin-3(2H)-one).

In line with the explanations above, this compound is useful for the treatment of heart diseases via the addressed target phosphodiesterase III. On the other hand it was desired to be taste masked. According to the underlying invention it is now possible to use this compound especially for oral medications, especially of taste sensitive animals like cats or dogs.

One preferred mode of the invention is a taste masked multi-layered particle according to the invention wherein the pharmaceutically active ingredient ($\delta$) (a cyclooxygenase 2 inhibitor) is meloxicam (4-hydroxy-2-methyl-N-(5-methyl-2-thiazolyl)-2H-1,2-benzothiazine-3-carboxamide-1,1-dioxide).

In line with the explanations above, this compound is especially useful for the treatment of inflammatory diseases via the addressed target cyclooxygenase 2. On the other hand it was desired to be taste masked. According to the underlying invention it is now possible to use this compound especially for oral medications, especially of taste sensitive animals like cats or dogs.

One preferred mode of the invention is a taste masked multi-layered particle according to the invention wherein the pharmaceutically active ingredient ($\epsilon$) (a benzodiazepine receptor agonist) is selected from 1-(4-chlorophenyl)-4-piperidinoimidazolin-2-one and imepitoin (1-(4-chlorophenyl)-4-(4-morpholinyl)-2,5-dihydro-1H-imidazol-2-one), preferably imepitoin.

In line with the explanations above, compounds of this group are useful for the treatment of central nervous system disorders, like epilepsy, especially idiopathic epilepsy, and behavioural abnormalities, esp. anxiety, of human and of animal patients via the addressed benzodiazepine receptor. On the other hand it was desired to be taste masked. According to the underlying invention it is now possible to use this compound especially for oral medications, especially of taste sensitive animals like dogs.

One aspect of the present invention resides in methods for the production of multi-layered particles according to the invention, in which the coating layers are assembled stepwise, starting from the material for the inert core, the single coating steps separated by drying steps.

As explained above, methods for the granulation process, i.e. for the subsequent addition of layers onto a smaller particle are per se known to the person skilled in the art. The claimed process starts with the core material, and the respective layer materials are added subsequently beginning with the innermost layer material. Each coating material is preferably added in liquid form, i.e. as a solution or suspension in a fluid carrier like water or other suitable solvents like ethanol or acetone or mixtures thereof, which liquid is allowed to dry subsequent to its application and before the next layer is added. The addition in powder form is also possible and especially appropriate for the final outermost layer or for additional intermediate layers.

With respect to the application of the intermediate coating layer (seal coating) (c) and of the outer coating layer (final or taste masking coating) (d), especially of the outer coating layer, it has been found that the intended coating materials are preferably applied to the respective particles in the form of a liquid solution or suspension in an appropriate solvent. This solvent can be selected from (purified) water or organic solvents like acetone, methanol, ethanol or dichloromethane or mixtures thereof. While the use of water is cost-efficient, the use of organic solvents may have the advantage of a faster drying step, thus shortening the time for the active ingredient to diffuse into the respective layer. Further, the choice of an organic solvent is especially preferred for pharmaceutically active ingredients with a high dissolution rate in water. The organic solvent then further hinders the diffusion of the active substance into outer layers during the layering step. Thus, by using organic solvents, it is possible to minimize migration of the active substance and thereby to ensure a very effective taste and/or odor masking. In addition, the layers that are produced with an organic solvent may be more tight than those produced with water and have an overall more even appearance. These however subtle differences may be exploited if the particles need to be optimized with respect to their dissolution behaviour vs. barrier function.

This effect is exemplified by the two examples of this application: the choice of both, water and organic liquids as a solvent, for the outermost layer of multi-layered particles comprising 1-[(3-cyano-pyridin-2-yl)methyl]-3-methyl-7-(2-butyn-1-yl)-8-[3-(R)-amino-piperidin-1-yl]-xanthine monohydrochloride as active ingredient are possible, with respect to the effect that an animal will not taste the respective active ingredient.

For the preparation of multi-layered particles comprising the drug cilobradine hydrochloride is has been found to be the best solution to apply the two outermost layers (i.e. the seal coating and the final coating) by use of organic solvents.

A person skilled in the art is able to analyze this effect and to modify the solvent, which might include the choice of an appropriate solvent mixture. For example the technique of Energy Dispersive X-ray analysis (EDS) can be used for analyzing to which extent the pharmaceutically active ingredient might still be present in the respective outer coating layer. This can be applied to the finally composed particles as well as for monitoring the production process by analyzing samples taken during the process.

A preferred method takes place in a fluid bed, preferably a Wurster fluid bed coating process (Wurster process).

Such a fluid bed is formed usually in a holding vessel when the solid particulate material is placed under appropriate conditions to cause the mixture to behave as a fluid. This is usually achieved by the introduction of pressurized fluid or gas like air through the particulate medium. This results in the medium then having many properties and characteristics of normal fluids, such as the ability to free-flow under gravity, or to be pumped using fluid type technologies. According to the invention the fluid bed can be used to spray the coating suspensions into the particulate material in order to achieve an overall tight coating layer around each particle.

Such a process is per se known to a person skilled in the art and can be applied with the aims and limitations given herein.

One preferred mode of the invention is such a method according to the invention, wherein the material for the outer coating layer (d) (i) (final or taste masking coating) is added to an amount of at least 50% (w/w) (based on the weight of the particles to be coated in this step), preferably 100 to 300% (w/w), more preferred 150 to 250% (w/w), even more preferred 180 to 220% (w/w), most preferred 190 to 210% (w/w).

As documented by example 1, this mode is especially advantageous for the addition of an coating layer (d) (i) (final or taste masking coating) that comprises poly(meth)acrylate or a comparable material, preferably basic butylated methacrylate copolymer, as explained above. It allows a good stability of the produced multi-layered particles, combined with a good dissolution profile.

One preferred mode of the invention is such a method according to the invention, wherein the material for the outer coating layer (d) (ii) (final or taste masking coating) is added to an amount of at least 25% (w/w) (based on the weight of the particles beneath this coating), preferably 25 to 100% (w/w), more preferred 50 to 90% (w/w), even more preferred 70 to 80% (w/w), most preferred 72.5 to 77.5% (w/w).

As documented by example 2, this mode is especially advantageous for the addition of an coating layer (d) (i) (final or taste masking coating) that comprises a mixture comprising 60-90% (w/w) ethylcellulose (EC) and 10-40% (w/w) HPMC, and respectively preferred embodiments thereof, as explained above.

As can be seen from the examples and the description above, it is one major achievement of the invention to provide coating materials that can be used for specific coating layers of particles comprising specific pharmaceutically active ingredients in order to exert an effective taste masking, accompanied with advantageous dissolution profiles and mechanical characteristics. Such advantageous coating materials and/or specific mixtures thereof have been developed for intermediate coating layers (seal coating) of such multi-layered particles as well as for outer coating layers (final or taste masking coating) of such multi-layered particles.

Accordingly, one aspect of the invention pertains to the use of
(i) a mixture comprising hydroxypropyl methylcellulose (HPMC) and polyethylene glycol (PEG) or
(ii) poly(1-vinylpyrrolidin-2-one) (PVP),
for the assembly of an intermediate coating layer (seal coating) (c) free from a low molecular weight water-soluble ionic compound of a multi-layered particle according to the invention.

Multi-layered particles comprising such materials for intermediate coating layers (seal coating) are exemplified by the examples and prove to be taste-masked, especially in combination with outer coating layers (final or taste masking coating) according to the invention.

One preferred use according to this aspect is a use wherein the material for the intermediate coating layer (seal coating) (c) (i) comprises 65 to 75% (w/w) HPMC, 7.5 to 12.5% (w/w) PEG 6000 and 19 to 23% (w/w) talc.

An alternative, not less preferred use according to this aspect is a use wherein the material for the intermediate coating layer (seal coating) (ii) comprises 70-80% (w/w) PVP and 20-25% (w/w) talc.

The advantages of such uses are presented in the examples and can be understood in the light of the description above. These are especially persistent in combination with the uses of further appropriate material for the outer coating layer according to the invention.

One equally preferred aspect of the invention pertains to the use of
(i) poly(meth)acrylate or
(ii) a mixture comprising 60-90% (w/w) EC and 10-40% (w/w) hydroxypropyl methylcellulose (HPMC),
for the assembly of an outer coating layer (final or taste masking coating) (d) free from a low molecular weight water-soluble ionic compound of a multi-layered particle according to the invention.

Multi-layered particles comprising such materials for outer coating layers (final or taste masking coating) are exemplified by the examples and prove to be taste-masked, especially in combination with intermediate coating layers (seal coating) according to the invention.

One preferred use according to this aspect is a use wherein the material for the outer coating layer (final or taste masking coating) comprises additional substances selected from flavoring agents, pigments and substances for the reduction of electrostatic charging.

For these allow the production of multi-layered particles according to the invention with the respective advantages of these materials that have already been explained above.

One preferred use according to this aspect is a use wherein the material for the outer coating layer (d) (i) (final or taste masking coating with poly(meth)acrylate) is added to an amount of at least 50% (w/w) (based on the weight of the particles to be coated in this step), preferably 100 to 300% (w/w), more preferred 150 to 250% (w/w), even more preferred 180 to 220% (w/w), most preferred 190 to 210% (w/w).

As explained above and documented by example 1, this mode allows a good stability of the produced multi-layered particles, combined with a good dissolution profile.

One not less preferred use according to this aspect is a use wherein the material for the outer coating layer (d) (ii) (final or taste masking coating with a mixture comprising 60-90% (w/w) EC and 10-40% (w/w) HPMC) is added to an amount of at least 25% (w/w) (based on the weight of the particles beneath this coating), preferably 25 to 100% (w/w), more preferred 50 to 90% (w/w), even more preferred 70 to 80% (w/w), most preferred 72.5 to 77.5% (w/w).

As explained above and documented by example 2, this mode allows a good stability of the produced multi-layered particles, combined with a good dissolution profile.

One aspect of the present invention provides the use of multi-layered particles according to the invention, for the treatment of
α) a metabolic disease, via DPP IV as target,
β) a heart disease, via the $i_f$-channel as target,
γ) a heart disease, via phosphodiesterase III as target,
δ) an inflammatory disease via cyclooxygenase 2 as target and/or
ε) a disease of the central nervous system via the benzodiazepine receptor as target.

Particles including respective pharmaceutically active ingredients comprised by them, are disclosed above. According to this aspect of the invention they can be used per se via oral application, i.e. without further excipients for the treatment of patients. For example they can be added to the food. Such a use has been made accessible by the invention of the multi-layered particles according to the invention because they are physically very stable, generally so stable that they stay intact even if the patient bites on it, e.g. during the ingestion of the food stuff A preferred use according to this aspect of the invention is such a use for the treatment of an animal.

For this purpose an appropriate amount of the respective material can be added to the animal's food stuff, e.g. by the persons taking care for the animals. This is very advantageous if the pharmaceutically active ingredient is intended to be used at a low dosage for prophylaxis against the respective diseases.

It is preferred that the particles used in this way comprise appropriate flavors in the outer coating. For example it has turned out to be useful to apply meat flavors in order to make the particles attractive for carnivorous animals.

One aspect of the present invention provides compositions comprising a multi-layered particle according to the invention.

In one aspect the present invention provides pharmaceutical compositions comprising a multi-layered particle according to the invention for the use in a method for the treatment of α) a metabolic disease, via DPP IV as target,
β) a heart disease, via the $i_f$-channel as target,
γ) a heart disease, via phosphodiesterase III as target,
δ) an inflammatory disease via cyclooxygenase 2 as target and/or
ε) a disease of the central nervous system via the benzodiazepine receptor as target.

In general, the multi-layered particles according to the invention can be incorporated in all forms of pharmaceutical compositions appropriate for the treatment of the respective diseases, preferably for oral administration. They can especially be incorporated into solid dosage forms like tablets as well as into predominantly liquid (e.g. oily suspensions) or pasteous dosage forms. Liquid or pasteous dosage forms in general offer the option of very flexible dosing by adjusting the administered volume. Tablets comprising multi-layered particles according to the invention can be divided without damaging the protective layer, hence also providing a possibility for dose adaption, e.g. by forming score lines.

It has been shown in acceptance tests that both, oily suspensions as well as tablets (both flavored) containing multi-layered particle according to the invention, lead to the desired result: they are very well accepted by the patients (exemplified by cats) and are in the majority of cases ingested voluntarily.

With respect to this aspect of the invention, the multi-layered particles are preferably sized in a way to generate an acceptable mouth feel for the patient (e.g. the cat), meaning: they are not be too big as that would lead to a gritty sensation which would lower the acceptance by the patient. Especially for the use in tablet mixtures, particles according to the invention are preferred that possess sufficient mechanical stability to resist compression as well as breaking or chewing of the resulting tablets. The film coating has preferably sufficient flexibility to allow deformation during a standard compression process.

Basically all sorts of additive materials that are suitable for such pharmaceutical dosage forms can be mixed with the multi-layered particles according to the invention in order to prepare a finally composed pharmaceutical, with respect to the envisaged application route and dosage regime of the respective patient group.

One preferred mode of the invention is a pharmaceutical composition according to the invention in solid form, preferably a capsule or tablet with a mass of 20 to 4000 mg per unit, more preferred 20 to 500 mg per unit, even more preferred 30 to 400 mg per unit, most preferred 40 to 300 mg per unit.

Solid dosage forms preferably comprise excipients that support the intended medical effect. Such other excipients are in general known to a person skilled in the art. Useful excipients are for example antiadherents (used to reduce the adhesion between the powder (granules) and the punch faces and thus prevent sticking to tablet punches), binders (solution binders or dry binders that hold the ingredients together), coatings (to protect further tablet ingredients from deterioration by moisture in the air and make large or unpleasant-tasting tablets easier to swallow), disintegrants (to allow the tablet to break upon dilution), fillers, diluents, flavours, colours, glidants (to promote powder flow by reducing inter-particle friction and cohesion), lubricants (to prevent ingredients from clumping together and from sticking to the tablet punches or capsule filling machine), preservatives, sorbents, sweeteners etc.

Preferred carriers and/or disintegrants are selected from the group of sugars and sugar alcohols, e.g. mannitol, lactose, starch, cellulose, microcrystalline cellulose and cellulose derivatives, e. g. methylcellulose, and the like.

Preferred binders are selected from the group consisting of polyvidone (used synonymously for povidone), methylcellulose, hydroxypropylmethylcellulose (HPMC), hydroxymethylcellulose, starch, gelatine, and the like.

Preferred ingredients are one or several flow regulators, e.g. selected from the group consisting of silica, preferably colloidal anhydrous silica, calcium silicate, magnesium silicate, talc, and the like.

Preferred disintegrants are selected from the group consisting of croscarmellose sodium, sodium starch glycolate, pregelatinised starch, cross-linked polyvinylpyrrolidone and the like.

Preferred lubricants selected from the group consisting of magnesium stearate, calcium stearate, glyceryl behenate, polyethylene glycol, stearic acid, talc and the like.

Preferred carriers are mannitol, starch and/or lactose. The carrier material can consist of coarse particles greater than 200 μm in size, equal or smaller than 200 μm in size, or spray-dried material.

Preferred starches are selected from the group consisting of corn (maize) starch, native starch, gelatinized starch, partly gelatinized starch, starch powder, starch granules, chemically modified starch and swellable physically modified starch.

As explained above, especially for the use in tablet mixtures, particles according to the invention have turned out to possess regularly sufficient mechanical stability to resist compression as well as breaking or chewing of the resulting tablets.

In order to secure these characteristics, it is preferred to incorporate multi-layered particles according to the invention with the following features:
  a size of the finally coated multi-layered particle between 0.08-0.8 mm, preferably 0.1-0.4 mm;
  applying a coating with sufficient flexibility, which can be based on the physical parameters of the polymer or by using appropriate plasticizers in appropriate amounts; and/or
  the use of microcrystalline cellulose pellets as core material, as these will undergo plastic deformation upon compression.

Further it is preferred to use an appropriate composition of the tableting mix—i.e. preferably using tableting excipients that undergo plastic deformation and ensuring that the mass ratio of coated pellets in the tableting mix does not exceed 50%, as demonstrated in the examples of this specification.

Such variations lie well within the ambit of the skilled person.

It is preferred to achieve a high load of the active ingredient (drug load) on the particles, because this influences the final size of the tablet. On the other hand a too high amount of multi-layered particles in the tableting mix could lead to an insufficient compressibility of the mix, resulting in mechanical instability of the tablets and an increased risk of disruption of the film due to excessive deformation of the pellets. Moreover, tablet disintegration and drug dissolution may be changed in an undesired way, e.g. too slow disintegration due to "sticking" of the pellets and/or too fast drug release than intended because of damages to the film.

The production of a pharmaceutical composition comprising 1-[(3-cyano-pyridin-2-yl)methyl]-3-methyl-7-(2-butyn-1-yl)-8-[3-(R)-amino-piperidin-1-yl]-xanthine monohydrochloride as pharmaceutically active ingredient is demonstrated by example 1, which in detail discloses the production of multi-layered particles containing the pharmaceutically active ingredient which particles were incorporated into a tablet formulation ready for the treatment of a patient.

An example of a completely composed tablet matrix and thus a preferred mode of carrying out the invention is disclosed in example 1. In addition to the drug containing multi-layered particles, the shown pharmaceutical composition contains other materials that are per se known from the state of the art and that can be adapted with respect to specific requirements, with respect to their nature as well as with respect to their concentration. This preferred collection of substances is intended to serve as filler and/or binder, disintegrant, flavoring agent, pigment, glidant and lubricant, respectively, as outlined in table 8. These functions correspond to the best knowledge at the time being but are in no way limiting the scope of the invention.

This composition contains especially a flavoring agent to render the tablets attractive to carnivorous animals. Especially this ingredient might be adapted with respect to the need of the pharmacists. For example, dogs and/or cats might prefer the meat flavor; other not predominantly carnivorous animals or humans might prefer another one.

As demonstrated by this example, multi-layered particles as well as pharmaceutical compositions, especially compressed tables comprising the multi-layered particles according to the invention fulfill all requirements regarding drug load and dissolution behavior. Especially the aqueous coating process for the final coating as described in example 1 worked surprisingly well with the water soluble drug substance 1-[(3-cyano-pyridin-2-yl)methyl]-3-methyl-7-(2-butyn-1-yl)-8-[3-(R)-amino-piperidin-1-yl]-xanthine monohydrochloride.

One preferred mode of the invention is a solid pharmaceutical composition according to the invention, comprising the pharmaceutically active ingredient in a final concentration of 0.1 to 1000 mg per unit, preferred 2 to 50 mg per unit, even more preferred 3 to 40 mg per unit, most preferred 4 to 30 mg per unit.

This has turned out to be useful for the intended therapy, e.g. the ones that are accessible by the preparations of the examples. The appropriate concentration can be adapted by a person skilled in the art with respect to the intended treatment and the patient group to be treated.

One preferred mode of the invention is a solid pharmaceutical composition according to the invention, in the form of a tablet, preferably a tablet with one or more score lines to be split into pieces.

The advantages of the tablet form have been explained above. The presence of one or more score lines on/in these tablets allows that the tablets be split into pieces in order to adapt the applied amount of the pharmaceutically active ingredient. This is especially worthy when a diverse patient population is envisaged, like companion animals that are characterized by a great number of races varying drastically with respect to the individual size, like dogs.

Another preferred mode of the invention is a pharmaceutical composition according to the invention in overall liquid form.

In some cases it is advantageous to prepare a pharmaceutical composition in a liquid formulation because this dosage form ensures a very precise dosing of the respective drug. Multi-layered particles according to the invention can be used for this application form.

The composition of an appropriate liquid formulation is per se known to a person skilled in the art. As exemplified by example 2, it is advantageous and accordingly preferred to use a mixture of triglycerides as basis and to add hydrophilic and/or hydrophobic colloidal silica in order to optimize the physicochemical properties of the composition.

Especially preferred is a mixture of hydrophilic and hydrophobic colloidal silica which ensures an appropriate viscosity behaviour of the suspension that remains more or less unchanged over the storage period. Commercially available siliciumdioxides (silica) are for example Aerosil® 200 (hydrophilic) and Aerosil® R972 (hydrophobic), both sold under these respective trade names by Evonik Röhm, Darmstadt, Germany.

During storage, such a suspension preferably exhibits a high viscosity, preventing sedimentation of the suspended multi-layered particles. If shaken, however, the viscosity of the suspension might transiently be lowered so that it can easily be applied via a syringe-like oral dispenser. This behaviour can for example be reached by the mentioned mixture of hydrophilic and hydrophobic colloidal silica.

It is further preferred that the composition contains a flavoring agent in order to render the formulation attractive for the patient, e.g. a meat flavor to render it attractive to carnivorous animals like cats.

With respect to cilobradine hydrochloride it is preferred to suspend the respective multi-layered particles in the liquid composition to an extent of about 3.8% (w/v), resulting in a concentration of 2 mg/ml of the pharmaceutically active ingredient.

If the coated particles are to be incorporated into a liquid matrix, it has to be ensured that the suspension medium does not interact with the film coating on the pellets in a way that would compromise the desired drug release profile. This is possible by the addition of another protective layer onto the surface of the particles, as explained above and/or by the addition of further excipients into the liquid matrix, as will be explained below. It is especially preferred to combine the respective teachings.

Another preferred mode of the invention is a pharmaceutical composition according to the invention in overall liquid form, which is an oily suspension, more preferred an oily suspension comprising a viscosity enhancer selected from one or more of silicon dioxide, hydrophobic silicon dioxide, EC (cellulose ether), poly(1-vinylpyrrolidin-2-one) (PVP), aluminium stearate, xanthan gum, carrageen, and/or starch derivatives.

Especially preferred are such overall liquid, oily pharmaceutical compositions that comprise a mixture of hydrophilic and hydrophobic colloidal siliciumdioxide, preferably at a weight percent ratio of 0.5:1 to 50:1, more preferred 1:1 to 25:1, more preferred 2:1 to 10:1, most preferred 2.25:1 to 5:1.

A person skilled in the art is able to vary the respective siliciumdioxide concentrations within these ranges. Regularly possible and preferred is a ratio and content of both compounds that gives the suspension a very advantageous physicochemical behavior, i.e. a high viscosity during storage and a lowered viscosity after shaking due to the mechanical energy exerted by the shaking. This effect stabilizes the suspension during its storage but allows that it can easily be applied after shaking, e.g. by a syringe or by dropwise addition to a food preparation etc.

Another preferred mode of the invention is a pharmaceutical composition according to the invention in overall liquid form, which is an aqueous suspension, more preferred an aqueous suspension comprising stabilisers selected from one or more of cellulose ethers, carbopol, xanthan gum, carrageen, microcrystalline cellulose.

Especially preferred are such overall liquid pharmaceutical compositions that comprise the pharmaceutically active ingredient in a final concentration of 0.1 to 20 mg/ml, preferred 0.5 to 5 mg/ml, more preferred 0.75 to 4 mg/ml, most preferred 0.5 to 3 mg/ml.

This has turned out to be useful for the intended therapy, e.g. the ones that are accessible by the preparations of the examples. The appropriate concentration can be adapted by a person skilled in the art with respect to the intended treatment and the patient group to be treated.

Preferred embodiments of this aspect of the invention are pharmaceutical compositions according to the invention, wherein the pharmaceutically active ingredient (a) (a DPP IV inhibitor) for the use for the treatment of a metabolic disease is selected from 1-[(3-cyano-pyridin-2-yl)methyl]-3-methyl-7-(2-butyn-1-yl)-8-[3-(R)-amino-piperidin-1-yl]-xanthine or any appropriate form and/or salt thereof, preferably 1-[(3-cyano-pyridin-2-yl)methyl]-3-methyl-7-(2-butyn-1-yl)-8-[3-(R)-amino-piperidin-1-yl]-xanthine monohydro chloride.

In line with the explanations above, these compounds have turned out to be very useful for the therapy of metabolic diseases of human and animal patients, of diabetes, especially of diabetes type 2, and in a certain dosage range that is accessible by the formulation intermediates according to the invention, i.e. by multi-layered particles according to the invention.

Respectively preferred are the following modes of this aspect of the invention:
 pharmaceutical compositions according to this aspect, for the treatment of an animal, preferably a mammal, more preferred a predominantly carnivorous mammal, most preferred a cat (feline);
 pharmaceutical compositions according to this aspect, for the treatment of diabetes, preferably of diabetes type 2;
 pharmaceutical compositions according to this aspect, in solid form, comprising 2 to 50 mg per unit, more preferred 3 to 40 mg per unit, even more preferred 4 to 30 mg per unit Equally preferred embodiments of this aspect of the invention are pharmaceutical compositions according to the invention, wherein the pharmaceutically active ingredient ((3) (an $i_f$-channel blocker) for the use for the treatment of a heart disease, especially heart failure via the $i_f$-channel as target is selected from zatebradine (1-(7,8-dimethoxy-1,3,4,5-tetrahydro-2H-3-benzazepin-2-on-3-yl)-3-[N-methyl-N-[(2-(3,4-dimethoxyphenyl)ethyl]amino]-propane), 3-[(N-(2-(3,4-dimethoxy-phenyl)-ethyl)piperidin-3-yl)-methyl]-(7,8-dimethoxy-1,3,4,5-tetrahydro-2H-3-benzazepin-2-on, its enantiomer cilobradine ((+)-3-[(N-(2-(3,4-dimethoxy-phenyl)ethyl)-piperidin-3-(S)-yl)-methyl]-(7,8-dimethoxy-1,3,4,5-tetrahydro-2H-3-benzazepin-2-on) or alinidine (2-(N-allyl-2,6-dichloro-anilino)-2-imidazoline), mostly preferred cilobradine hydrochloride ((+)-3-[(N-(2-(3,4-dimethoxyphenyl)ethyl)-piperidin-3-(S)-yl)-methyl]-(7,8-dimethoxy-1,3,4,5-tetrahydro-2H-3-benzazepin-2-on hydrochloride).

In line with the explanations above, these compounds have turned out to be very useful for the therapy of heart diseases, especially of congestive heart failure of human and animal patients, and in a certain dosage range that is accessible by the formulation intermediates according to the invention, i.e. by multi-layered particles according to the invention.

Respectively preferred are the following modes of this aspect of the invention:
 pharmaceutical compositions according to this aspect, for the treatment of an animal, preferably a mammal, more preferred a predominantly carnivorous mammal, most preferred a cat (feline);
 pharmaceutical compositions according to this aspect, in overall liquid form, comprising the pharmaceutically active ingredient in a final concentration of 0.5 to 5 mg/ml, preferred 0.75 to 4 mg/ml, more preferred 0.5 to 3 mg/ml.

Equally preferred embodiments of this aspect of the invention are pharmaceutical compositions according to the invention, wherein the pharmaceutically active ingredient (γ) (a phosphodiesterase III inhibitor) for the use for the treatment of a heart disease via phosphodiesterase III as target, is pimobendan ((RS)-6-[2-(4-methoxyphenyl)-1H-benzimidazol-5-yl]-5-methyl-4,5-dihydropyridazin-3 (2H)-one).

A preferred mode of this aspect is such a pharmaceutical composition for the treatment of an animal, preferably a mammal, more preferred a predominantly carnivorous mammal, most preferred a dog (canis) or a cat (feline).

Equally preferred embodiments of this aspect of the invention are pharmaceutical compositions according to the invention, wherein the pharmaceutically active ingredient (6) (a cyclooxygenase 2 inhibitor) for the use for the treatment of an inflammatory disease via cyclooxygenase 2 as target, is meloxicam 4-hydroxy-2-methyl-N-(5-methyl-2-thiazolyl)-2H-1,2-benzothiazine-3-carboxamide-1,1-dioxide).

A preferred mode of this aspect is such a pharmaceutical composition for the treatment of an animal, preferably a mammal, more preferred a predominantly carnivorous mammal, most preferred a dog (canis) or a cat (feline).

Equally preferred embodiments of this aspect of the invention are pharmaceutical compositions according to the invention, wherein the pharmaceutically active ingredient (ε) (a benzodiazepine receptor agonist) for the use for the treatment of a disease of the central nervous system via the benzodiazepine receptor as target, is selected from 1-(4-chlorophenyl)-4-piperidinoimidazolin-2-one and imepitoin (1-(4-chlorophenyl)-4-(4-morpholinyl)-2,5-dihydro-1H-imidazol-2-one), preferably imepitoin.

In line with the explanations above, these compounds have turned out to be very useful for the therapy of central nervous system disorders like epilepsy, especially idiopathic epilepsy, and behavioural abnormalities, esp. anxiety, of human and animal patients, and in a certain dosage range that is accessible by multi-layered particles according to the invention.

Respectively preferred are the following modes of this aspect of the invention:
 pharmaceutical compositions according to this aspect, for the treatment of an animal, preferably a mammal, more preferred a predominantly carnivorous mammal, most preferred a dog (canis);
 pharmaceutical compositions according to this aspect, for the treatment of epilepsy and/or anxiety, preferably of epilepsy, more preferred of idiopathic epilepsy;
 pharmaceutical compositions according to this aspect, that allow the oral administration of up to 60 mg/kg per day, preferably 5 to 40 mg/kg per day;
 pharmaceutical compositions according to this aspect, that are administered not more than five times daily, preferably once or twice daily.

Another aspect of the invention pertains to the package of an overall liquid, oily pharmaceutical composition according to the invention comprising a glass vial and the pharmaceutical composition filled therein.

Especially this package form has turned out to be useful for the storage of overall liquid, oily pharmaceutical composition according to the invention because they strongly inhibit the diffusion of humidity through the walls of the respective vial into the overall water-free pharmaceutical composition.

It is further preferred that a dark glass, e.g. green or even better: brown glass is used, in order to further protect the ingredients, e.g. against the light.

Appropriate sizes for such glass vials can be developed by a person skilled in the art with respect to the amount to be filled in, e.g. for single use, for providing an appropriate amount for the complete therapy of one patient or for the treatment of a patient group, for example a breed of domestic animals.

One subject of the invention pertains to pharmaceutical compositions comprising cilobradine ((+)-3-[(N-(2-(3,4-dimethoxy-phenyl)ethyl)-piperidin-3-(S)-yl)-methyl]-(7,8-dimethoxy-1,3,4,5-tetrahydro-2H-3-benzazepin-2-on), cilobradine hydrochloride ((+) -3-[(N-(2-(3,4-dimethoxy-phenyl)ethyl)-piperidin-3-(S)-yl)-methyl]-(7,8-dimethoxy-1,3,4,5-tetrahydro-2H-3-benzazepin -2-on hydrochloride), zatebradine (1-(7,8-dimethoxy-1,3,4,5-tetrahydro-2H-3-benzazepin-2-on-3-yl)-3-[N-methyl-N-[(2-(3,4-dimethoxyphenyl)ethyl]amino]-propane), or alinidine (2-(N-allyl-2,6-dichloro-anilino)-2-imidazoline) for use in a method for the treatment of a heart disease of an animal, preferably a mammal, more preferred a predominantly carnivorous mammal, even more preferred a cat (feline) or dog (canis), most preferred a cat (feline).

In line with the explanations above, cilobradine or cilobradine hydrochloride are preferred, more preferred is cilobradine hydrochloride.

In line with the explanations given above, it has been found by the inventors that especially this compound that addresses the $i_f$-channel as its respective target is highly advantageous for the treatment of heart diseases of such animals.

Accordingly, another aspect of the invention is the use of cilobradine ((+)-3-[(N -(2-(3,4-dimethoxy-phenyl)ethyl)-piperidin-3-(S)-yl)-methyl]-(7,8-dimethoxy-1,3,4,5-tetrahydro-2H-3-benzazepin-2-on), cilobradine hydrochloride ((+)-3-[(N-(2-(3,4-dimethoxy-phenyl)ethyl)-piperidin-3-(S)-yl)-methyl]-(7,8-dimethoxy-1,3,4,5-tetrahydro-2H-3-benzazepin -2-on hydrochloride), zatebradine (1-(7,8-dimethoxy-1,3,4,5-tetrahydro-2H-3-benzazepin-2-on-3-yl)-3-[N-methyl-N-[(2-(3,4-dimethoxyphenyl)ethyl]amino]-propane), or alinidine (2-(N-allyl-2,6-dichloro-anilino)-2-imidazoline) in a method for the treatment of a heart disease of an animal, preferably a mammal, more preferred a predominantly carnivorous mammal, even more preferred a cat (feline) or dog (canis), most preferred a cat (feline).

In line with the explanations above, cilobradine or cilobradine hydrochloride are preferred, more preferred is cilobradine hydrochloride.

According to a further aspect, it is preferred to use the multi-layered particles described above for the treatment of heart diseases, especially heart failure of companion animals, predominantly carnivorous animals like cats (feline) or dogs (canine), e.g. by incorporation into a respective medical formulation.

Preferred is the use of liquid pharmaceutical compositions with a final concentration of the active ingredient of 0.5 to 5 mg/ml, preferred 0.75 to 4 mg/ml, more preferred 0.5 to 3 mg/ml.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Formulation of a Compound for the Treatment of Diabetes

An objective of this example was to produce a formulation of compound 1-[(3-cyano-pyridin-2-yl)methyl]-3-methyl-7-(2-butyn-1-yl)-8-[3-(R)-amino-piperidin-1-yl]-xanthine monohydrochloride, as disclosed e.g. by patent application PCT/EP2011/054440, in the form of a tablet with an overall weight of 180-260 mg with a dose of 21.68 mg of 1-[(3-cyano-pyridin-2-yl)methyl]-3-methyl-7-(2-butyn-1-yl)-8-[3-(R)-amino-piperidin-1-yl]-xanthine monohydro chloride, which corresponds to 20 mg of the respective free base.

A four-step process was applied as summarized in Table 2 and in more detail below.

TABLE 2

Flow chart for the production of multi-layered particles comprising 1-[(3-cyano-pyridin-2-yl)methyl]-3-methyl-7-(2-butyn-1-yl)-8-[3-(R)-amino-piperidin-1-yl]-xanthine monohydrate as an active ingredient.

| step | starting material | coating | result |
|---|---|---|---|
| 1 | inert core particles | drug layering with pharmaceutically ingredient and HPMC | IR1 pellets |
| 2 | IR1 pellets | drug layering with pharmaceutically active ingredient and HPMC | IR2 pellets |
| 3 | IR2 pellets | seal coating with HPMC and PEG 6000 | SC (seal coated) pellets |
| 4 | SC pellets | taste masking coating with poly(meth)acrylate | final multi-layered particle |

Steps 1 and 2: Drug Layering (Production of IR1 and IR2 Pellets)

Particles of microcrystalline cellulose of about 400 g with an average diameter of 100 µm (100 µm Cellets®; purchased from Syntapharm; Harke Group, Mülheim an der Ruhr, Germany) were placed in a fluid bed apparatus (Glatt, Binzen, Germany). For the first layering step, a mixture of 600 g of 1-[(3-cyano-pyridin-2-yl)methyl]-3-methyl-7-(2-butyn-1-yl)-8-[3-(R)-amino-piperidin-1-yl]-xanthine monohydrochloride and 90 g of HPMC (apparent viscosity 4.8-7.2 mPa*s at 2% (w/v) in water at 20° C.; (commercially available under the trade name Pharmacoat® 606 from ShinEtsu, Tokyo, Japan), i.e. at a ratio of about 15% (w/w)), was dissolved in purified water at a concentration of about 20% (w/v) and sprayed onto the inert carrier material and subsequently dried. According to the geometry of the apparatus, the resulting IR1 pellets were split into two fractions and treated identically according to step 2.

In step 2, 400 g of IR1 pellets were placed in the same fluid bed apparatus as before and sprayed with the same mixture of 600 g active ingredient and 90 g HPMC that was used in step 1. The total composition of the resulting IR2 pellets is shown in Table 3.

TABLE 3

Composition of IR2 pellets comprising 1-[(3-cyano-pyridin-2-yl)-methyl]-3-methyl-7-(2-butyn-1-yl)-8-[3-(R)-amino-piperidin-1-yl]-xanthine monohydrochloride as the active ingredient.

| Component | Total amount [% (w/w)] |
|---|---|
| inert core particles (Cellets ® 100) | 13.46 |
| active ingredient | 75.25 |
| HPMC (Pharmacoat ® 606) | 11.29 |

Step 3: Seal Coating (Production of SC Pellets)

The resulting IR2 pellets of step 2 were covered by a protective layer ("seal coating") to produce so-called SC pellets as follows: a mixture of 168 g of HPMC (apparent viscosity 2.4-3.6 mPa*s at 2% (w/v) in water at 20° C. (commercially available under the trade name Pharmacoat 603 ® from ShinEtsu, Tokyo, Japan), 21 g PEG 6000 and 50 g talc, dispersed in purified water to yield about 11% (w/v) solids in the spraying liquid, was sprayed onto the IR2 pellets (600 g) in the same fluid bed apparatus as used for steps 1 and 2 and subsequently dried. The resulting total composition of the SC pellets is given in Table 4.

TABLE 4

Composition of SC pellets comprising 1-[(3-cyano-pyridin-2-yl)-methyl]-3-methyl-7-(2-butyn-1-yl)-8-[3-(R)-amino-piperidin-1-yl]-xanthine monohydrochloride as active ingredient.

| Component | Total amount [% (w/w)] |
|---|---|
| inert core particles (Cellets ® 100) | 10.77 |
| active ingredient | 60.19 |
| HPMC (Pharmacoat ® 606) | 9.03 |
| HPMC (Pharmacoat ® 603) | 14.04 |
| PEG 6000 | 1.77 |
| Talc | 4.20 |

Step 4: Final Coating (Taste Masking; Production of Final Multi-Layered Particles), Aqueous Coating As in the steps before the following mixture was added to the SC pellets: 62.5% (w/w) basic butylated methacrylate copolymer (certain poly(meth)acrylate, which is a cationic copolymer based on dimethylaminoethyl methacrylate, butyl methacrylate, and methyl methacrylate with a ratio of 2:1:1 and a molecular weight of about 47,000 g/mol (sold under the trade name Eudragit® E PO by Evonik Röhm, Darmstadt, Germany), 6.2% (w/w) sodium lauryl sulfate, 9.3% (w/w) stearic acid and 21.9% (w/w) magnesium stearate, dispersed in purified water to yield approximately 16% (w/v) solids in the spraying liquid.

This process was carried out in four different modes, differing with respect to the thickness of the added final coating:
(a) stopping the process after adding 50% final coating material, calculated on the weight amount of SC pellets placed in the fluid bed chamber (50% coating level)
(b) stopping the process after adding 100% final coating material, respectively (100% coating level)
(c) stopping the process after adding 150% final coating material, respectively (150% coating level)
(d) stopping the process after adding 200% final coating material, respectively (200% coating level)
Accordingly, the final coating consists of a mixture of basic butylated methacrylate copolymer, sodium lauryl sulphate, stearic acid, and magnesium stearate in the relative portions of 62.5/6.2/9.3/21.9 (all in % (w/w)) with around 50%, 100%, 150% and 200% solid deposit (weight percentage based on the amount of "SC pellets" starting material).

The total composition of final taste masked multi-layered particles comprising 1-[(3-cyano-pyridin-2-yl)methyl]-3-methyl-7-(2-butyn-1-yl)-8-[3-(R)-amino-piperidin-1-yl]-xanthine monohydrochloride as the active ingredient, as produced by steps 1 to 4 with stopping the final coating process after adding 200% final coating material (i.e. mode (d); 200% coating level), is given in Table 5.

TABLE 5

Total composition of final taste masked multi-layered particles comprising 1-[(3-cyano-pyridin-2-yl)methyl]-3-methyl-7-(2-butyn-1-yl)-8-[3-(R)-amino-piperidin-1-yl]-xanthine monohydrochloride as the active ingredient.

| Component | Amount [% (w/w)] | Function |
|---|---|---|
| inert core particles (Cellets ® 100) | 3.59 | Carrier |
| pharmaceutically active ingredient | 20.06 | Drug layer |
| HPMC (Pharmacoat ® 606) | 3.01 | |
| HPMC (Pharmacoat ® 603) | 4.69 | Seal coating |
| PEG 6000 | 0.59 | |
| Talc | 1.40 | |
| basic butylated methacrylate copolymer | 41.66 | Final coating |
| Sodium dodecylsulfate | 4.15 | (taste masking) |
| Stearic acid | 6.26 | |
| Magnesium stearate | 14.59 | |

Even with this highly water soluble drug, all drug layering and polymer coating steps could be performed using aqueous as well as organic solvent coating processes without the bitter active ingredient migrating into the outer polymer layers. This lack of admixing was proven by SEM coupled with x-ray/EDS (Energy Dispersive X-ray analysis) which showed that no chloride ions stemming from the pharmaceutically active ingredient were detected in the final outer coating layer.

In a further control experiment, the raman spectra of components of the particle were measured. It was found that the final coating layer comprising the butylated methacrylate copolymer at 200% coating level showed a thickness of between 77 and 119 µm±10 µm.

Variation of Step 4: Final Coating (Taste Masking Coating; Production of Final Multi-Layered Particles), Organic Solvent Coating In a variation of the aqueous coating, step 4 was repeated identically, except that an organic solvent coating was applied. For this purpose, 444 g basic butylated methacrylate copolymer in powder form (Eudragit® E PO) and 186 g magnesium stearate were dissolved in isopropanol/acetone (volume ratio 3:2) to yield approximately 17% (w/v) solids in the spraying liquid. The final coating material was sprayed onto the SC pellets, which had been placed in the fluid bed apparatus like before.

Again, the process was carried out in 4 different modes, differing with respect to the thickness of the added final coating, leading to the comparably composed materials (a) to (d), i.e. to multi-layered particles comprising a final coating consisting of basic butylated methacrylate copolymer and magnesium stearate in a 70.5/29.5 ratio (all in % (w/w)) with around 50%, 100%, 150% and 200% solid deposit (weight percentage based on the amount of "SC pellets" starting material).

Dissolution Experiments after Final Aqueous Coating

The final multi-layered particles produced according to the above steps, with step 4 comprising the aqueous coating process, were analyzed with respect to their dissolution characteristics.

The respective particles, prototypes (a), (b), (c), and (d), differing with respect to the thickness of the final coating level, were analyzed in a dissolution apparatus 2, according to European Pharmacopoeia (Ph. Eur.), using either $Na_2HPO_4$ buffer (pH 6.8) or hydrochloric acid (pH 1) as dissolution medium. The dissolution samples were analyzed for the active ingredient via HPLC/UV.

Figure 1B:
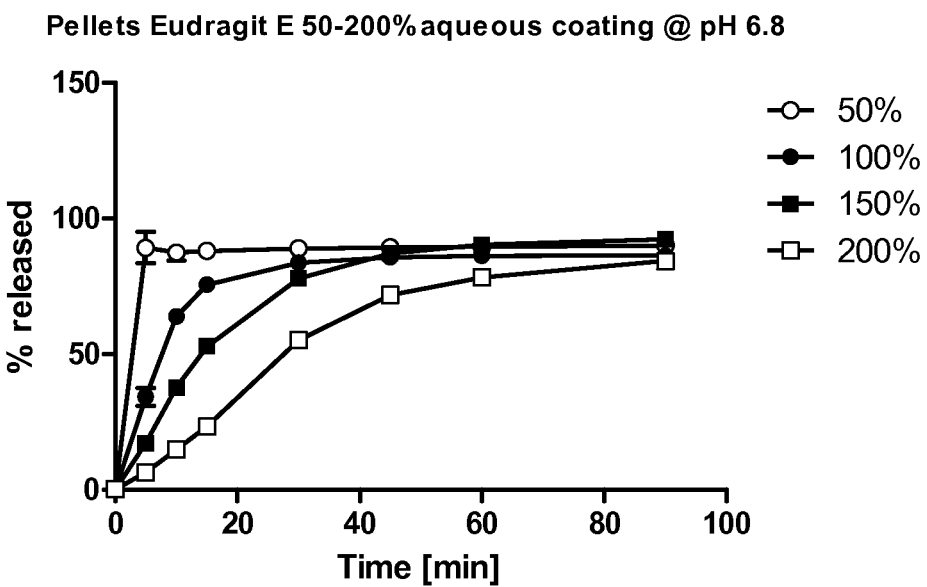

The dissolution experiment was carried out at two different pH values, at pH 6.8 and pH 1, to mimic the pH environment in the patient's oral cavity and stomach, respectively. The result is given in Table 6 and corresponding FIG. 1. FIG. 1A shows the measured dissolution curve at pH 1 and FIG. 1B shows the measured dissolution curve at pH 6.8. The amount of the released drug was normalized to the theoretical drug content in the sample, which allows maximal values higher than 100% and are comparable with each other for each curve. The result becomes clear with respect to the finally reached plateau for each curve (which theoretically can also be used for the definition of 100% release).

TABLE 6

Drug release from multi-layered particles comprising 1-[(3-cyano-pyridin-2-yl)methyl]-3-methyl-7-(2-butyn-1-yl)-8-[3-(R)-amino-piperidin-1-yl]-xanthine monohydrochloride finally coated with basic butylated methacrylate copolymer at 50-200% coating level (aqueous spraying process) at pH 1 and pH 6.8 (mean, n ≥ 3) measured values are the cumulative percentage of released material after the respective time (visualized in FIGS. 1A and 1B).

| Time [min] | 50% coating | 100% coating | 150% coating | 200% coating |
|---|---|---|---|---|
| pH 1 | | | | |
| 0 | 0 | 0 | 0 | 0 |
| 5 | 87.0 | 81.0 | 69.0 | 78.8 |
| 10 | 87.1 | 82.4 | 92.3 | 83.4 |
| 15 | 87.6 | 92.1 | 113.7 | 101.8 |
| 30 | 87.9 | 91.9 | 124.6 | 104.9 |
| 45 | 87.9 | 93.7 | 131.3 | 107.4 |
| 60 | 88.0 | 93.9 | 135.9 | 108.7 |
| 90 | 88.0 | 93.2 | 145.0 | 110.4 |
| pH 6.8 | | | | |
| 0 | 0 | 0 | 0 | 0 |
| 5 | 82.7 | 31.7 | 17.1 | 5.8 |
| 10 | 85.9 | 61.4 | 37.6 | 14.3 |
| 15 | 86.7 | 72.3 | 52.8 | 22.2 |
| 30 | 87.6 | 80.8 | 77.8 | 53.0 |
| 45 | 88.2 | 83.0 | 86.8 | 70.4 |
| 60 | 88.6 | 83.5 | 89.5 | 77.0 |
| 90 | 89.7 | 84.0 | 91.5 | 83.4 |

Dissolution Experiments after Final Organic Solvent Coating

The final multi-layered particles produced according to the steps before with step 4 varied with respect to the coating process, i.e. the variant of organic solvent coating, were also analyzed with respect to their dissolution characteristics.

Figure 2A:
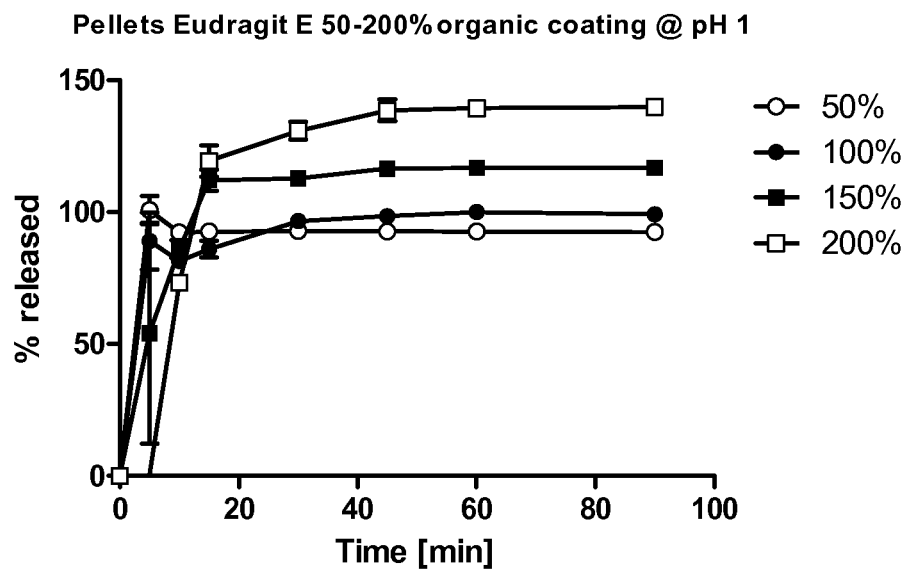
FIG. 2: Dissolution curves at pH 1 (FIG. 2A) and pH 6.8 (FIG. 2B) from multi-layered particle prototypes coated with basic butylated methacrylate copolymer, produced according to Example 1, at different coating levels (organic solvent process). (Means±SD, n≥3, are shown).
Figure 2B:
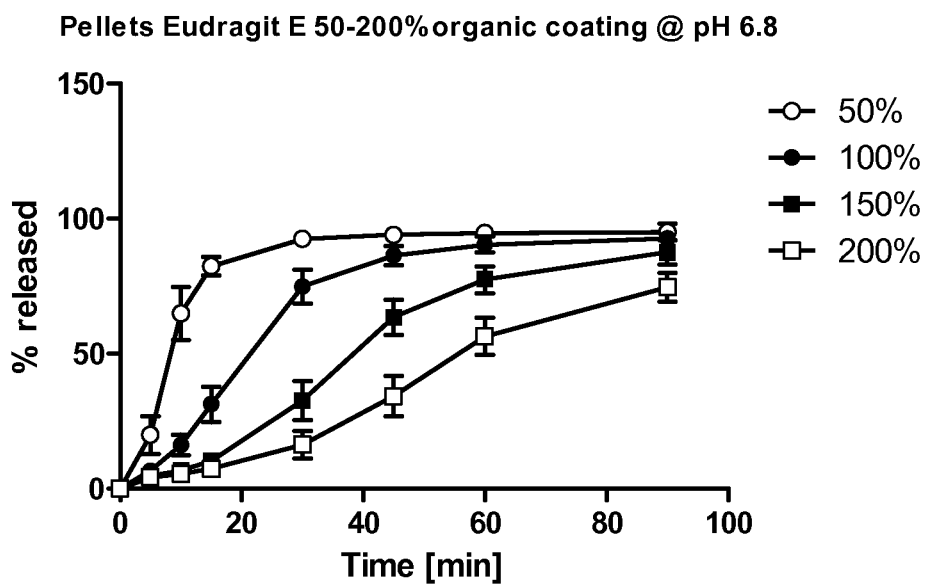

For this purpose, the respective particles, prototypes (a), (b), (c) and (d), differing with respect to the thickness of the final coating level, were treated as before. The dissolution experiment was again carried out at the two different pH values of pH 6.8 and pH 1. The result is given in Table 7 and corresponding FIG. 2. FIG. 2A shows the measured dissolution curve at pH 1 and FIG. 2B shows the measured dissolution curve at pH 6.8.

TABLE 7

Drug release from multi-layered particles comprising 1-[(3-cyano-pyridin-2-yl)methyl]-3-methyl-7-(2-butyn-1-yl)-8-[3-(R)-amino-piperidin-1-yl]-xanthine monohydrochloride finally coated with basic butylated methacrylate copolymer at 50-200% coating level (organic spraying process) at pH 1 and pH 6.8 (mean, n ≥ 3) measured values are the total percentage of released material after the respective time (visualized in FIGS. 2A and B).

| Time [min] | 50% coating | 100% coating | 150% coating | 200% coating |
|---|---|---|---|---|
| pH 1 | | | | |
| 0 | 0 | 0 | 0 | 0 |
| 5 | 100.7 | 89.1 | 54.0 | 54.0 |
| 10 | 92.2 | 81.5 | 86.0 | 86.0 |
| 15 | 92.6 | 85.9 | 112.1 | 112.1 |
| 30 | 92.8 | 96.6 | 112.8 | 112.8 |
| 45 | 92.7 | 98.4 | 116.5 | 116.5 |
| 60 | 92.6 | 100.0 | 116.6 | 116.6 |
| 90 | 92.4 | 99.1 | 116.6 | 116.6 |
| pH 6.8 | | | | |
| 0 | 0 | 0 | 0 | 0 |
| 5 | 19.9 | 6.7 | 4.7 | 4.3 |
| 10 | 64.9 | 16.2 | 6.9 | 5.6 |
| 15 | 82.5 | 31.3 | 10.4 | 7.4 |
| 30 | 92.5 | 74.9 | 32.7 | 16.3 |
| 45 | 94.0 | 86.5 | 63.6 | 34.3 |
| 60 | 94.7 | 90.4 | 77.5 | 56.4 |
| 90 | 95.1 | 92.7 | 87.6 | 74.6 |

Result of the Dissolution Experiments

Both of these data sets reveal that multi-layered particles coated with basic butylated methacrylate copolymer exhibit an increasingly delayed release at pH 6.8, depending on the coating thickness, and an immediate release at pH 1. Accordingly, they are able to mask the taste of a pharmaceutically active ingredient in the oral cavity (pH 6.8) while facilitating immediate drug release in the stomach (pH 1).

This is true for the particles that have been coated by an aqueous coating process with the material basic butylated methacrylate copolymer, sodium lauryl sulphate, stearic acid and magnesium stearate in the 62.5/6.2/9.3/21.9 mixture (all in % (w/w) as well as for the particles that have been coated by an organic solvent coating process with the material basic butylated methacrylate copolymer and magnesium stearate in a 70.5/29.5 ratio (all in % (w/w)).

Especially particles coated at coating levels of about 200% show the desired drug release profile, irrespective of the solvent used for the final coating process.

Tablet Formulation

Multi-layered particles comprising 1-[(3-cyano-pyridin-2-yl)methyl]-3-methyl-7-(2-butyn-1-yl)-8-[3-(R)-amino-piperidin-1-yl]-xanthine monohydrochloride coated with basic butylated methacrylate copolymer at a 200% coating level according to the aqueous coating procedure described before, were admixed to a complete tablet formulation, according to the composition outlined in table 8. The listed ingredients were bought from commercial providers. Colloidal silicium dioxide was bought under the trade name Aerosil® 200 from Evonik Röhm, Darmstadt, Germany. Cross-linked PVP was bought under the trade name Kollidon® CL from BASF, Ludwigshafen, Germany).

TABLE 8

Composition of tableting mix containing taste masked multi-layered particles comprising 1-[(3-cyano-pyridin-2-yl)-methyl]-3-methyl-7-(2-butyn-1-yl)-8-[3-(R)-amino-piperidin-1-yl]-xanthine monohydrochloride coated with basic butylated methacrylate copolymer at a 200% coating level.

| Component | Amount [% (w/w)] | Function |
|---|---|---|
| final multi-layered particles comprising pharmaceutically active ingredient and a 200% coat | 49.78 | API containing intermediate |
| Mannitol | 27.42 | filler/binder |
| Maize starch | 9.50 | filler/binder |
| cross-linked PVP (Kollidon ® CL) | 1.50 | disintegrant |
| Meat flavor | 10.00 | flavoring agent |
| Iron oxide yellow | 0.35 | pigment |
| Iron oxide brown | 0.35 | pigment |
| colloidal silicium dioxide (Aerosil ® 200) | 0.30 | glidant |
| Magnesium stearate | 0.80 | lubricant |

All components except for the multilayered particles were screened together, placed in a polyethylene bag and premixed by hand. The multilayered particles were screened separately. The components were subsequently put in a 40 l mixing container and mixed to yield the final tableting mix. By use of a standard apparatus the tableting mix was compressed to tablets with 5, 10 and 20 mg of the pharmaceutically active ingredient.

Dissolution Experiments with the Tablet

The tablets produced as described before were analyzed in a dissolution experiment. This dissolution experiment was carried out as described before for the particles, again at the two different pH values of pH 6.8 and pH 1. As a control, the multi-layered particles comprising a 200% poly(meth)acrylate aqueous coating as described before were measured in the same way. The measurement aimed at the detection of the released drug, quantified by HPLC/UV (percentage in relation to the total amount of the active ingredient in the tablet).

Figure 3A:
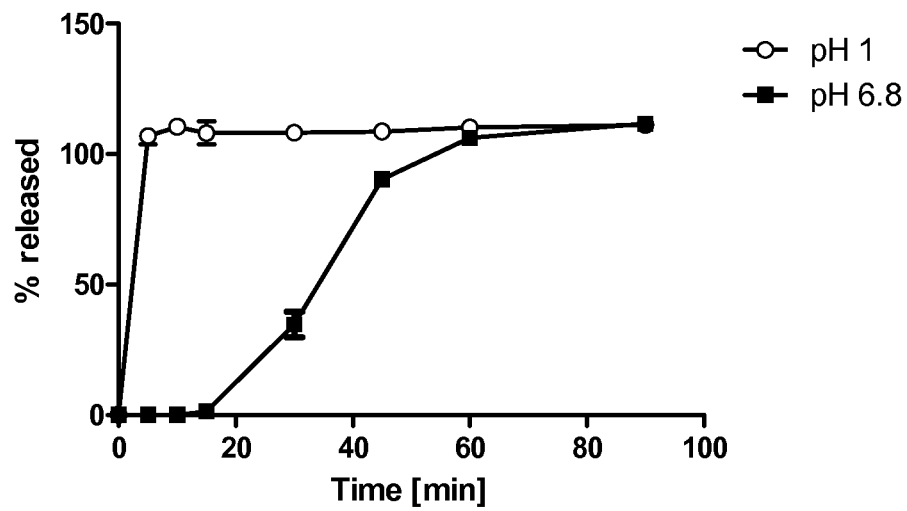
FIG. 3: Dissolution curves at pH 1 and pH 6.8 of active ingredient from multi-layered particles with 200% poly(meth)acrylate aqueous coating (FIG. 3A) and from the derived tablets (FIG. 3B) produced according to Example 1. (Means±SD, n≥3, are shown).
Figure 3B:
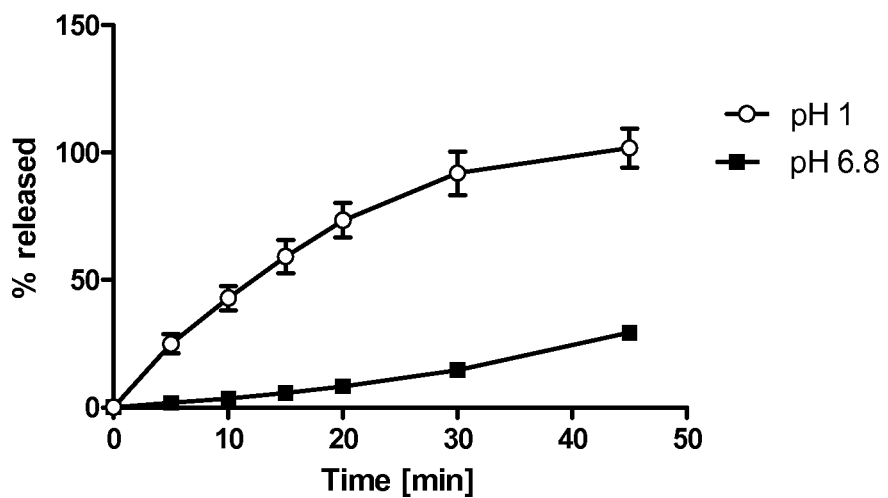

The result is given in following table 9 and corresponding FIG. 3.

TABLE 9

Drug release from multi-layered particles comprising 1-[(3-cyano-pyridin-2-yl)methyl]-3-methyl-7-(2-butyn-1-yl)-8-[3-(R)-amino-piperidin-1-yl]-xanthine monohydrochloride coated with basic butylated methacrylate copolymer at a 200% coating level at pH 1 and pH 6.8 and of the derived tablets (mean ± SD, n ≥ 3); measured values are the total percentage of released active compound after the respective time (visualized in FIG. 3).

| Time [min] | % released at pH 1 | % released at pH 6.8 |
|---|---|---|
| Multi-layered particles | | |
| 0 | 0 | 0 |
| 5 | 106.9 | 0 |
| 10 | 110.5 | 0.1 |
| 15 | 108.1 | 1.3 |
| 30 | 108.2 | 34.7 |
| 45 | 108.6 | 90.4 |
| 60 | 110.2 | 106.2 |
| 90 | 111.2 | 111.7 |
| Tablets | | |
| 0 | 0 | 0 |
| 5 | 24.9 | 1.8 |
| 10 | 42.9 | 3.5 |
| 15 | 59.2 | 5.7 |
| 20 | 73.5 | 8.2 |
| 30 | 91.9 | 14.7 |
| 45 | 101.9 | 29.3 |

As can be seen from these data, the release of the active ingredient from tablets containing the drug loaded pellets is slower than from uncompressed pellets at pH 6.8 as well as at pH 1, due to the disintegration of the tablet.

Further, the film coating on the multi-layered particles is mechanically stable enough to stay intact throughout the tableting process and can provide taste and/or odor masking of the drug in a tablet formulation.

EXAMPLE 2

Formulation of a Compound for the Treatment of a Heart Disease

This example aims at the formulation of compound (+)-3-[(N-(2-(3,4-dimethoxy-phenyl)ethyl)-piperidin-3-(S)-yl)-methyl]-(7,8-dimethoxy-1,3,4,5-tetrahydro-2H-3-benzazepin-2-on hydrochloride in liquid form.

For the production of multi-layered particles for incorporation into a liquid dosage form, a three-step process was applied which process is summarized in table 10.

TABLE 10

Flow chart for the production of multi-layered particles according to the invention, comprising (+)-3-[(N-(2-(3,4-dimethoxy-phenyl)ethyl)-piperidin-3-(S)-yl)-methyl]-(7,8-dimethoxy-1,3,4,5-tetrahydro-2H-3-benzazepin-2-on hydrochloride as active ingredient.

| step | starting material | coating | result |
|---|---|---|---|
| 1 | inert core particles | drug layering with pharmaceutically active ingredient and HPMC/magnesium stearate | IR pellets |
| 2 | IR pellets | seal coating with PVP K 30/Talc/colloidal siliciumdioxide | SC (seal coated) pellets |
| 3 | SC pellets | taste masking coating with EC/HPMC/magnesium stearate/colloidal siliciumdioxide | final multi-layered particle |

Step 1: Drug Layering

Like in example 1 microcrystalline cellulose particles with an average diameter of 100 µm were used as starting material and layered with active ingredient and binder, using water as solvent. The layer material consisted of 66.6% (w/w) of the pharmaceutically active ingredient, 31.7% (w/w) HPMC (Pharmacoat® 606; see example 1) and 1.7% (w/w) magnesium stearate, dispersed in purified water to yield approx. 19% solids in the spraying liquid.

The resulting composition of the produced IR pellets is given in table 11.

TABLE 11

Composition of IR pellets comprising (+)-3-[(N-(2-(3,4-dimethoxy-phenyl)ethyl)-piperidin-3-(S)-yl)-methyl]-(7,8-dimethoxy-1,3,4,5-tetrahydro-2H-3-benzazepin-2-on hydrochloride

| Component | Amount [% (w/w)] |
|---|---|
| inert core particles (Cellets ® 100) | 80.94 |
| pharmaceutically active ingredient | 12.70 |
| HPMC (Pharmacoat ® 606) | 6.04 |
| Magnesium stearate | 0.32 |

Step 2: Seal Coating

The IR pellets produced in step 1 were further processed in the same apparatus by spraying the seal coating onto the IR pellets. The material for the seal coating was composed of PVP K 30 (commercially available by the provider BASF, Ludwigshafen, Germany, under the trade name Kollidon® 30/talc, at a weight-percent ratio of 75.4:22.5, dispersed in a 94:6 mixture (m/m) of acetone and ethanol. 0.5% (w/w) of a highly disperse (colloidal) silicium dioxide (Aerosil® 200, commercially available from Evonik) was added by an additional (intermediate step) to the seal coated material after the application of the PVP K 30/talc mixture and drying of the organic solvent.

The total composition of the SC (seal coated) pellets yielded in this step (cilobradine seal coated pellets) is given in table 12.

TABLE 12

Composition of SC pellets comprising (+)-3-[(N-(2-(3,4-dimethoxy-phenyl)ethyl)-piperidin-3-(S)-yl)-methyl]-(7,8-dimethoxy-1,3,4,5-tetrahydro-2H-3-benzazepin-2-on hydrochloride

| Component | Amount [% (w/w)] |
|---|---|
| IR pellets comprising the pharmaceutically active ingredient | 76.54 |
| PVP K 30 (Kollidon ® 30) | 17.67 |
| Talc | 5.29 |
| colloidal silicium dioxide (Aerosil ® 200) | 0.5 |

Step 3: Final Coating (Taste Masking Coating)

The SC pellets produced in step 2 were further processed in the same apparatus by spraying the final coating onto the SC pellets. The material for the final taste and/or odor masking coating was composed of EC/HPMC/magnesium stearate at a weight-percent ratio of 55.2:23.8:19.8 (the ratio of EC/HPMC in the film coating being about 70:30). For this purpose, EC, HPMC and magnesium stearate were dispersed in a 1:1 mixture (v/v) of methanol and dichloromethane, and sprayed onto the SC pellets.

The coating was applied to a thickness of 75% based on the initial amount of SC pellets.

Like in step 2, 0.5% of the colloidal silica of Aerosil® 200 were added to the final product before sieving.

The chosen EC was Ethocel® 45 cps STD Premium, commercially available from Dow Chemical, Schwalbach, Germany. The chosen HPMC for this layer was Methocel® E5 Premium LV, commercially available from Dow Chemical. Aerosil® 200 was provided by Evonik.

The overall composition of the final multi-layered particles is given in table 13.

TABLE 13

Composition of final multi-layered particles comprising (+)-3-[N-(2-(3,4-dimethoxy-phenyl)ethyl)-piperidin-3-(S)-yl)-methyl]-(7,8-dimethoxy-1,3,4,5-tetrahydro-2H-3-benzazepin-2-on hydrochloride

| Component | Amount [% (w/w)] |
|---|---|
| SC pellets comprising the pharmaceutically active ingredient | 56.86 |
| EC | 23.86 |
| HPMC | 10.25 |
| Magnesium stearate | 8.54 |
| colloidal silicium dioxide (Aerosil ® 200) | 0.5 |

Table 14 discloses the detailed overall composition of taste masked multi-layered particles comprising (+)-3-[(N-(2-(3,4-dimethoxy-phenyl)ethyl)-piperidin-3-(S)-yl)-methyl]-(7,8-dimethoxy-1,3,4,5-tetrahydro-2H-3-benzazepin-2-on hydrochloride, as produced according to steps 1-3 of this example, along with the assumed physicochemical function of the respective material.

TABLE 14

Detailed composition of final multi-layered particles comprising (+)-3-[(N-(2-(3,4-dimethoxy-phenyl)ethyl)-piperidin-3-(S)-yl)-methyl]-(7,8-dimethoxy-1,3,4,5-tetrahydro-2H-3-benzazepin-2-on hydrochloride

| Component | Amount [% (w/w)] | Function |
|---|---|---|
| inert core particles (Cellets ® 100) | 35.23 | Carrier |
| pharmaceutically active ingredient cilobradine (calculated as hydrochloride) | 5.53 | Drug layer |
| HPMC | 2.63 | |
| Polyvinylpyrrolidone K 30 | 10.05 | Seal coating |
| Talc | 3.01 | |
| Ethylcellulose | 23.86 | Final coating |
| HPMC | 10.25 | (taste masking) |
| Magnesium stearate | 8.68 | |
| colloidal silicium dioxide (Aerosil ® 200) | 0.78 | Reduction of electrostatic charging in seal coating and final coating |

Dissolution Experiments

The multi-layered particles produced in this example were tested with respect to their dissolution properties in the same way as the particles according to example 1, again at the two different pH values of 6.8 and 1. Measured values are the total percentage of released material after the respective time, normalized to the theoretical drug content. The result is given in table 15 and visualized in FIG. 4.

TABLE 15

Figure 4:
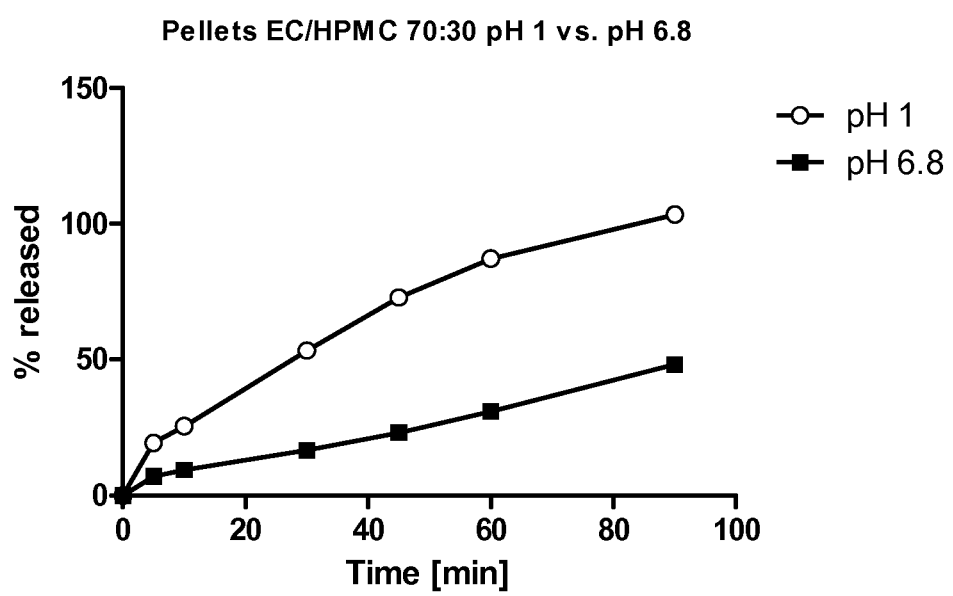
FIG. 4: Dissolution curves at pH 1 and pH 6.8 from multi-layered particle prototypes coated with EC/HPMC 70:30, according to Example 2. (Means±SD, n≥3, are shown).

Drug release from multi-layered particles comprising (+)-3-[(N-(2-(3,4-dimethoxy-phenyl)ethyl)-piperidin-3-(S)-yl)-methyl]-(7,8-dimethoxy-1,3,4,5-tetrahydro-2H-3-benzazepin-2-on hydrochloride finally coated with EC/HPMC 70:30 at pH 1 and pH 6.8 (mean, n ≥ 3; visualized in FIG. 4)

| Time [min] | % released at pH 1 | % released at pH 6.8 |
|---|---|---|
| 0 | 0.0 | 0.0 |
| 5 | 19.4 | 7.2 |
| 10 | 25.6 | 9.4 |
| 30 | 53.4 | 16.7 |
| 45 | 72.9 | 23.2 |

TABLE 15-continued

Drug release from multi-layered particles comprising (+)-3-
[(N-(2-(3,4-dimethoxy-phenyl)ethyl)-piperidin-3-(S)-yl)-
methyl]-(7,8-dimethoxy-1,3,4,5-tetrahydro-2H-3-benzazepin-
2-on hydrochloride finally coated with EC/HPMC 70:30 at pH 1
and pH 6.8 (mean, n ≥ 3; visualized in FIG. 4)

| Time [min] | % released at pH 1 | % released at pH 6.8 |
|---|---|---|
| 60 | 87.2 | 30.9 |
| 90 | 103.4 | 48.3 |

According to these data, the dissolution from EC/HPMC coated pellets is delayed, therefore providing efficient taste and/or odor masking of the bitter drug (+)-3-[(N-(2-(3,4-dimethoxy-phenyl)ethyl)-piperidin-3-(S)-yl)-methyl]-(7,8-dimethoxy-1,3,4,5-tetrahydro-2H-3-benzazepin-2-on hydrochloride. This could be verified by acceptance tests with laboratory cats with the derived completely formulated liquid composition prepared as described below.

Usually, EC/HPMC films show a sustained release behavior that is independent of pH. In this case, however, the product surprisingly showed a slower release at pH 6.8 which is favorable with regards to the invention, i.e. providing efficient taste masking in the oral cavity and a faster release in the acidic stomach. This may be explained by the lipophilicity profile of the active substance cilobradine HCl, which is slightly more lipophilic at neutral pH values. This, together with the coating applied, may have led to a slower release.

Liquid Pharmaceutical Composition

In order to prepare a liquid pharmaceutical composition, the final multi-layered particles comprising the active ingredient ciloradine prepared in the way explained above were incorporated into an oily liquid. This liquid consisted of a mixture of Medium chain triglycerides (Miglyol® 821, bought from Sasol, Hamburg, Germany), a hydrophilic colloidal silicium dioxide (Aerosil® 200, Evonik), a hydrophobic colloidal silicium dioxide (Aerosil® R972, Evonik) and meat flavor, at the weight ratios listed in table 16.

TABLE 16

Liquid pharmaceutical composition comprising multi-layered
particles comprising (+)-3-[(N-(2-(3,4-dimethoxy-phenyl)-
ethyl)-piperidin-3-(S)-yl)-methyl]-(7,8-dimethoxy-1,3,4,5-
tetrahydro-2H-3-benzazepin-2-on hydrochloride

| Component | Amount [% (w/w)] |
|---|---|
| medium chain triglycerides (Miglyol ® 821) | 93.23 |
| hydrophilic colloidal silicium dioxide (Aerosil ® 200) | 4.44 |
| hydrophobic colloidal silicium dioxide (Aerosil ® R972) | 1.82 |
| meat flavor | 0.51 |

The multi-layered particles as produced according to step 3 were suspended in the mentioned liquid composition to an amount of about 3.8% (w/v), resulting in a concentration of 2 mg/ml of the pharmaceutically active ingredient (calculated as hydrochloride).

It has been found that the composition of the oily solvent, especially the mixture of hydrophilic and hydrophobic colloidal silica, ensures an appropriate viscosity behaviour of the suspension that remains more or less unchanged over the storage period. During storage, the suspension exhibits a high viscosity, preventing sedimentation of the suspended cilobradine pellets. If shaken, the viscosity of the suspension is transiently lowered so that it can easily be applied via a syringe-like oral dispenser.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

To the extent that the patents and publications referred to herein provide exemplary procedural or other details supplementary to those set forth herein, all of these patents and publications are specifically incorporated herein by reference. Nothing herein is to be construed as an admission that the invention is not entitled to antedate such disclosure by virtue of prior invention.

What is claimed is:

1. A pharmaceutical composition comprising a taste masked multi-layered particle, the multi-layered particle comprising:
   a) an inert core,
   b) at least one coating layer that comprises a pharmaceutically active ingredient and a binder,
   c) an intermediate coating layer (seal coating) free from a low molecular weight water-soluble ionic compound and comprising a water-soluble pharmaceutical film-forming compound, selected from the group consisting of hydroxypropyl methylcellulose (HPMC), polyethylene glycol (PEG) poly(1-vinylpyrrolidin-2-one) (PVP), and any combination thereof, and
   d) an outer coating layer (final or taste masking coating) free from a low molecular weight water-soluble ionic compound and comprising
      (i) a poly(meth)acrylate or
      (ii) a mixture comprising 60-90% (w/w) ethylcellulose (EC) and 10-40% (w/w) hydroxypropyl methylcellulose (HPMC),
   wherein the pharmaceutically active ingredient is water-soluble and comprises either at least one basic group and/or a bitter taste;
   wherein the pharmaceutical composition is in solid form with a mass of 20 to 4000 mg per unit.

2. The pharmaceutical composition of claim 1, further comprising the pharmaceutically active ingredient in a final concentration of 0.1 to 1000 mg per unit.

3. The pharmaceutical composition of claim 1 in the form of a tablet with one or more score lines to be split into pieces.

4. The pharmaceutical composition of claim 1 in a liquid form.

5. The pharmaceutical composition of claim 4, wherein the liquid form comprises an oily suspension comprising a viscosity enhancer selected from the group consisting of silicon dioxide, hydrophobic silicon dioxide, EC (cellulose ether), poly(1-vinylpyrrolidin-2-one) (PVP), aluminium stearate, xanthan gum, carrageen, starch derivatives, and one or more combinations thereof.

6. The pharmaceutical composition of claim 5, further comprising a mixture of hydrophilic and hydrophobic colloidal silicium dioxide.

7. The pharmaceutical composition of claim 6 which is an aqueous suspension comprising stabilizers selected from one or more of cellulose ethers, carbopol, xanthan gum, carrageen, microcrystalline cellulose.

8. The pharmaceutical composition of claim 4, further comprising the pharmaceutically active ingredient in a final concentration of 0.1 to 20 mg/ml.

9. A package of an overall liquid, oily pharmaceutical composition according to claim 5 comprising a glass vial and the pharmaceutical composition filled therein.

* * * * *